United States Patent
Yukawa et al.

(10) Patent No.: US 10,017,791 B2
(45) Date of Patent: Jul. 10, 2018

(54) CORYNEFORM BACTERIUM TRANSFORMANT AND PROCESS FOR PRODUCING 4-HYDROXYBENZOIC ACID OR SALT THEREOF USING THE SAME

(71) Applicant: GREEN PHENOL DEVELOPMENT CO., LTD., Kyoto (JP)

(72) Inventors: Hideaki Yukawa, Kyoto (JP); Masayuki Inui, Kyoto (JP); Kazumi Hiraga, Kyoto (JP); Masako Suda, Kyoto (JP); Ryoma Hashimoto, Kyoto (JP)

(73) Assignee: GREEN CHEMICALS CO., LTD., Kyoto (JP)

( * ) Notice: Subject to any disclaimer, the term of this patent is extended or adjusted under 35 U.S.C. 154(b) by 0 days.

(21) Appl. No.: 15/302,020

(22) PCT Filed: Apr. 7, 2015

(86) PCT No.: PCT/JP2015/060805
§ 371 (c)(1),
(2) Date: Oct. 5, 2016

(87) PCT Pub. No.: WO2015/156271
PCT Pub. Date: Oct. 15, 2015

(65) Prior Publication Data
US 2017/0114374 A1    Apr. 27, 2017

(30) Foreign Application Priority Data

Apr. 8, 2014   (JP) ................................. 2014-079504

(51) Int. Cl.
C12N 1/20    (2006.01)
C12P 7/42    (2006.01)
(Continued)

(52) U.S. Cl.
CPC .................. *C12P 7/42* (2013.01); *C12N 1/20* (2013.01); *C12N 9/88* (2013.01); *C12N 15/52* (2013.01); *C12Y 401/0304* (2013.01)

(58) Field of Classification Search
None
See application file for complete search history.

(56) References Cited

U.S. PATENT DOCUMENTS 6,030,819 A    2/2000   Amaratunga et al.
6,114,157 A    9/2000   Johnson et al.
(Continued)

FOREIGN PATENT DOCUMENTS

EP    3 147 360    3/2017
JP    2012-183048    9/2012
(Continued)

OTHER PUBLICATIONS

International Preliminary Report on Patentability dated Oct. 12, 2016 in International Application No. PCT/JP2015/060805.
(Continued)

*Primary Examiner* — Richard C Ekstrom
(74) *Attorney, Agent, or Firm* — Wenderoth, Lind & Ponack, L.L.P.

(57) ABSTRACT

A transformant constructed by introducing a gene which encodes an enzyme having chorismate-pyruvate lyase activity into a coryneform bacterium as a host is capable of efficiently producing 4-hydroxybenzoic acid or a salt thereof from a sugar. When the transformant is cultured under aerobic conditions where the transformant does not grow, 4-hydroxybenzoic acid or a salt thereof can be produced in a particularly efficient manner.

4 Claims, 1 Drawing Sheet

(51) Int. Cl.
*C12N 9/88* (2006.01)
*C12N 15/52* (2006.01)

(56) References Cited

U.S. PATENT DOCUMENTS

| | | | |
|---|---|---|---|
| 6,210,937 B1* | 4/2001 | Ward | C12N 15/52 435/146 |
| 2013/0273624 A1 | 10/2013 | Yukawa et al. | |
| 2016/0273005 A1* | 9/2016 | Magnus | C12N 9/88 |

FOREIGN PATENT DOCUMENTS

| WO | 2012/063862 | 5/2012 |
|---|---|---|
| WO | 2014/105796 | 7/2014 |

OTHER PUBLICATIONS

International Search Report dated Jun. 16, 2015 in International Application No. PCT/JP2015/060805.
Brian P. Nichols et al., "Cloning and Sequencing of *Escherichia coli* ubiC and Purification of Chorismate Lyase", Journal of Bacteriology, 1992, vol. 174, No. 16, pp. 5309-5316.
Marion Siebert et al., "Formation of 4-hydroxybenzoate in *Escherichia coli*: characterization of the ubiC gene and its encoded enzyme chorismate pyruvate-lyase", Microbiology, 1994, vol. 140, pp. 897-904.
R. Müller et al., "Microbial production of specifically ring-$^{13}$C-labelled 4-hydroxybenzoic acid", Applied Microbiology and Biotechnology, 1995, vol. 43, pp. 985-988.
Jessica L. Barker et al., "Microbial Synthesis of p-Hydroxybenzoic Acid from Glucose", Biotechnology and Bioengineering, 2001, vol. 76, No. 4, pp. 376-390.
GenBank Accession No. CP003488.1, Jan. 31, 2014.
GenBank Accession No. CU928158.2, Dec. 16, 2008.
GenBank Accession no. CP001796, Jan. 31, 2014.
GenBank Accession No. CP004091, Jan. 31, 2014.
GenBank Accession No. CP002824. Jan. 31, 2014.
GenBank Accession No. CP004345, Jan. 30, 2014.
GenBank Accession No. CU633749, Mar. 26, 2008.
Partial Supplementary European Search Report dated Dec. 14, 2017 in corresponding European patent application No. 15776134.7.
Yan Huang et al., "Genetic and biochemical characterization of a 4-hydroxybenzoate hydroxylase from *Corynebacterium glutamicum*", Applied Microbiology and Biotechnology, vol. 78, No. 1, 2008, pp. 75-83.
Extended European Search Report dated Mar. 28, 2018 in corresponding European patent application No. 15776134.7.
Database Uniprot [Online] Feb. 19, 2014 (Feb. 19, 2014), Weinstock, G. et al.: "RecName: Full=Chorismate pyruvate-lyase; Short=CL; Short=CPL; EC=4.1.3.40", XP002778996, Database accession No. D1P752.
Database UniProt [Online] Feb. 19, 2014 (Feb. 19, 2014), Sudarsanam, P. et al.: "RecName: Full=Chorismate pyruvate-lyase; Short=CL; Short=CPL; EC=4.1.3.40", XP002778997, Database accession No. B2Q559.
Database UniProt [Online] Feb. 19, 2014 (Feb. 19, 2014), Galac, M.R. & Lazzaro, B.P.: "RecName: Full=Chorismate pymvate-lyase; Short=CL; Short=CPL; EC=4.1.3.40", XP002778998, Database accession No. K8VZZ4.
Database UniProt [Online] Feb. 19, 2014 (Feb. 19, 2014), Sudarsanam, P. et al.: "RecName: Full=Chorismate pyruvate-lyase; Short=CL; Short=CPL; EC=4.1.3.40", XP002778999, Database accession No. B6XE56.
Database UniProt [Online] Feb. 19, 2014 (Feb. 19, 2014), Galac, M.R. & Lazzaro, B.P.: "RecName: Full=Chorismate pymvate-lyase; Short=CL; Short=CPL; EC=4.1.3.40", XP002779000, Database accession No. K8VY45.
Database UniProt [Online] Feb. 19, 2014 (Feb. 19, 2014), Kucerova, E. et al.: "RecName: Full=Chorismate pyruvate-lyase; Short=CL; Short=CPL; EC=4.1.3.40", XP002779001, Database accession No. A7MPN9.

* cited by examiner

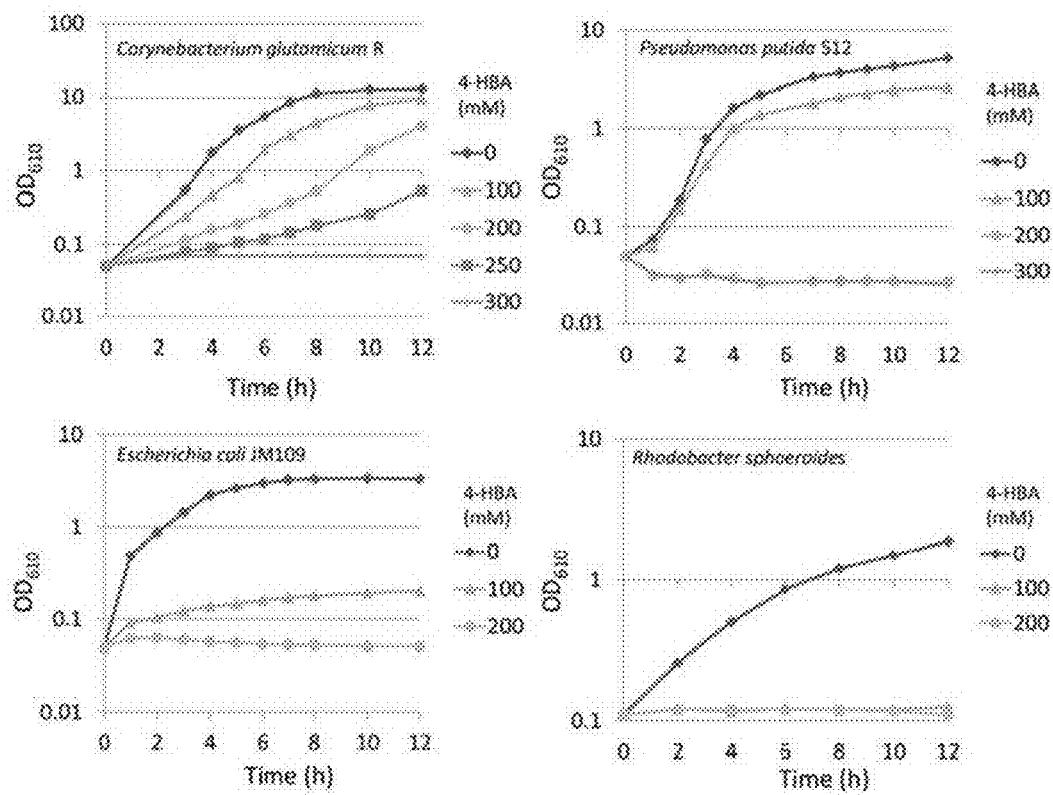

CORYNEFORM BACTERIUM TRANSFORMANT AND PROCESS FOR PRODUCING 4-HYDROXYBENZOIC ACID OR SALT THEREOF USING THE SAME

TECHNICAL FIELD

The present invention relates to a coryneform bacterium transformant which is constructed by specific gene recombination so as to have an ability to produce 4-hydroxybenzoic acid or a salt thereof (hereinafter may be abbreviated as "4-HBA"), and relates to an efficient 4-HBA-producing process using the transformant.

BACKGROUND ART

Against the backdrop of global warming and exhaustion of fossil resources, production of chemical products using renewable resources, along with production of biofuels, is recognized as an emerging industry, biorefinery, which is an important means for realizing a low-carbon society, and has attracted attention.

4-Hydroxybenzoic acid is a useful substance as a raw material used to synthesize paraben, which is an antimicrobial agent, and also as a raw material for liquid-crystal polymers. Currently, 4-HBA is produced by chemical conversion from crude oil as a raw material. Examples of chemical 4-HBA production methods include a method in which phenol, potassium hydroxide, and carbon dioxide are reacted under high-pressure conditions. These methods depend on fossil materials for phenol as the starting material, and in addition, are energy-consumptive production processes requiring high-temperature and high-pressure conditions, which processes are typical in the chemical industry. Therefore, there is a need to establish an energy-saving, environment-conscious process that allows production of 4-HBA from renewable resources and produces less waste products, that is, to establish 4-HBA bioproduction technologies.

However, conventional bioproduction of 4-HBA from renewable resources is less productive as compared to bioproduction of lactic acid or ethanol because the metabolic reaction from a raw material sugar consists of a great many steps. In addition, there are problems, such as inhibition of bacterial growth by produced 4-HBA and cytotoxicity of 4-HBA. Therefore, industrial production of 4-HBA has not been achieved.

Using *Escherichia coli*, it has been revealed that 4-HBA is synthesized from chorismic acid, which is an intermediate in the shikimate pathway involved in the synthesis of aromatic amino acids etc., by chorismate-pyruvate lyase encoded by ubiC (Non Patent Literature 1 and 2, Patent Literature 1 and 2).

There is a report of introduction of a chorismate pyruvate-lyase gene (ubiC) of *Escherichia coli* into a different kind of microorganism, *Klebsiella pneumoniae* in an attempt to produce 4-HBA (Non Patent Literature 3). Also, there is a report of fermentative production of 4-HBA in an *Escherichia coli* in which the shikimic acid pathway is reinforced (Non Patent Literature 4). Furthermore, in an attempt to avoid the growth inhibition or the toxic action by 4-HBA, there are reports of selection of 4-HBA-resistant strains and of culture in the presence of an ion-exchange resin, but practically sufficient productivity of 4-HBA has not been achieved. Meanwhile, the inventors have released a report on the introduction of chorismate-pyruvate lyase into a coryneform bacterium and the production of phenol from glucose using the transformed coryneform bacterium. However, there is no description regarding the production of 4-HBA or the enzyme activity of chorismate-pyruvate lyase (Patent Literature 3).

Regarding other ubiC than that of *Escherichia coli*, the ubiC of *Rhodobacter sphaeroides* has been reported. However, both the transformant in which ubiC is highly expressed in *Escherichia coli* as a host and the transformant in which ubiC is highly expressed in *Rhodobacter sphaeroides* as a host are capable of producing 4-HBA only at low concentrations, and therefore, are not practically satisfactory (Patent Literature 4).

The UbiC of *Escherichia coli* has already been enzymatically analyzed in detail, and is known to be strongly inhibited by the product, 4-HBA. Therefore, in order to establish a high 4-HBA-producing strain that is industrially useful, obtaining a highly active ubiC, obtaining a resistant ubiC against product inhibition by 4-HBA, and selecting a 4-HBA resistant host are extremely important.

CITATION LIST

Patent Literature

Patent literature 1: U.S. Pat. No. 6,030,819
Patent literature 2: U.S. Pat. No. 6,114,157
Patent literature 3: WO 2012/063862
Patent literature 4: JP 2012-183048 A

Non Patent Literature

Non Patent literature 1: J. Bacteriol., 174, 5309-5316 (1992)
Non Patent literature 2: Microbiology, 140, 897-904 (1994)
Patent literature 3: Appl. Microbiol. Biotechnol., 43, 985-988 (1995)
Patent literature 4: Biotechnol. Bioeng., 76, 376-390 (2001)

SUMMARY OF INVENTION

Technical Problem

An object of the present invention is to provide a microorganism capable of efficiently producing 4-HBA from a sugar, a compound that can be metabolized into chorismic acid, or chorismic acid; and a process for efficiently producing 4-HBA using the microorganism.

Solution to Problem

The present inventors have wholeheartedly carried out investigations in order to achieve the object described above and obtained the finding that a transformant constructed by introducing a chorismate-pyruvate lyase gene, which catalyzes the production of 4-HBA from chorismic acid, into a coryneform bacterium can efficiently produce 4-HBA from glucose or the like.

The present inventors also found that the transformant has a particularly higher 4-HBA productivity when the reaction is performed under aerobic conditions where the transformant substantially does not grow.

In addition, using a number of hosts of transformants that had been reported to produce 4-HBA, the inventors made comparisons regarding the effect of 4-HBA on the growth of the hosts, and found that, among *Escherichia coli*, *Rhodobacter sphaeroides*, *Corynebacterium glutamicum*, and

*Pseudomonas putida* (reported as a solvent-resistant bacterium), *Corynebacterium glutamicum* has the highest resistance to 4-HBA.

The present invention, which has been completed based on the above-mentioned findings, provides the following transformants and processes for producing 4-HBA.

[1] A transformant capable of producing 4-hydroxybenzoic acid or a salt thereof, the transformant being constructed by introducing a gene which encodes an enzyme having chorismate-pyruvate lyase activity into a coryneform bacterium as a host.

[2] The transformant of the above [1], wherein the gene which encodes an enzyme having chorismate-pyruvate lyase activity is a gene of the genus *Pantoea*, the genus *Providencia*, the genus *Escherichia*, the genus *Pseudoalteromonas*, the genus *Cronobacter*, the genus *Citrobacter*, the genus *Enterobacter*, the genus *Pseudomonas*, the genus *Morganella*, the genus *Azotobacter*, the genus *Shewanella*, or the genus *Cupriavidus*.

[3] The transformant of the above [1], wherein the gene which encodes an enzyme having chorismate-pyruvate lyase activity is a gene of *Pantoea ananatis*, *Providencia rustigianii*, *Providencia stuartii*, *Providencia sneebia*, *Providencia rettgeri*, *Providencia alcalifaciens*, *Providencia burhodogranariea*, *Escherichia coli*, *Escherichia fergusonii*, *Pseudoalteromonas piscicida*, *Pseudoalteromanas haloplanktis*, *Cronobacter sakazakii*, *Citrobacter youngae*, *Citrobacter koseri*, *Enterobacter aerogenes*, *Enterobacter cloacae*, *Pseudomonas putida*, *Morganella morganii*, *Azotobacter vinelandii*, *Shewanella putrefaciens*, or *Cupriavidus taiwanensis*.

[4] The transformant of the above [1], wherein the gene which encodes an enzyme having chorismate-pyruvate lyase activity is the DNA of the following (a) or (b).
(a) a DNA consisting of any one of the base sequences of SEQ ID NOs: 1 to 21
(b) a DNA which hybridizes to a DNA consisting of a complementary base sequence of any one of the DNAs of (a) under stringent conditions or which consists of a base sequence having 90% or more of homology with any one of the base sequences of (a), and which encodes a polypeptide having chorismate-pyruvate lyase activity

[5] The transformant of any one of the above [1] to [4], wherein the coryneform bacterium as the host is a *Corynebacterium*.

[6] The transformant of the above [5], wherein the *Corynebacterium* as the host is *Corynebacterium glutamicum*.

[7] The transformant of the above [6], wherein the *Corynebacterium glutamicum* as the host is *Corynebacterium glutamicum* R (FERM BF-18976), ATCC13032, or ATCC13869.

[8] *Corynebacterium glutamicum* HBA-2 (Accession Number: NITS BP-01838), which is a transformant of *Corynebacterium glutamicum*.

[9] A process for producing 4-hydroxybenzoic acid or a salt thereof, which comprises a step of culturing the transformant of any one of the above [1] to [8] in a reaction mixture containing at least one starting compound selected from the group consisting of a sugar, a compound from which the transformant is capable of producing chorismic acid by metabolism, and chorismic acid, and a salt thereof, and a step of recovering 4-hydroxybenzoic acid or a salt thereof from the reaction mixture.

[10] The process of the above [9], wherein the transformant is cultured under aerobic conditions where, the transformant does not grow.

Advantageous Effects of Invention

Using the transformant of the present invention, 4-HBA can be efficiently produced from a sugar such as glucose, chorismic acid, quinic acid, shikimic acid, or the like.

Generally, growth of microorganisms is inhibited by an aromatic compound, such as 4-HBA, because of its cytotoxicity, and therefore 4-HBA production using microorganisms was difficult. Also, the chorismate-pyruvate lyase activity of a microorganism is generally weak and chorismate-pyruvate lyase is strongly inhibited by the product, 4-HBA. Therefore, production of a sufficient quantity of 4-HBA was difficult. According to the present invention, however, by the use of a microorganism that is highly resistant to 4-HBA, the production of 4-HBA can be achieved with a practically sufficient efficiency.

BRIEF DESCRIPTION OF DRAWINGS

FIG. 1 shows the effect of 4-hydroxy benzoate on the growth of four kinds of microorganisms (*Corynebacterium glutamicum* R, *Escherichia coli* JM109, *Pseudomonas putida* S12 ATCC700801, and *Rhodobacter sphaeroides* NBRC12203).

DESCRIPTION OF EMBODIMENTS

Hereinafter, the present invention will be described in detail.
(1) 4-HBA-Producing Transformant
The transformant of the present invention capable of producing 4-HBA is a transformant constructed by introducing a gene which encodes an enzyme having chorismate-pyruvate lyase activity into a coryneform bacterium as a host.
Host
The coryneform bacteria are a group of microorganisms defined in Sergey's Manual of Determinative Bacteriology, Vol. 8, 599 (1974), and are not particularly limited as long as they grow under normal aerobic conditions.

The specific examples include the genus *Corynebacterium*, the genus *Brevibacterium*, the genus *Arthrobacter*, the genus *Mycobacterium* and the genus *Micrococcus*. Among the coryneform bacteria, the genus *Corynebacterium* is preferred.

Examples of the genus *Corynebacterium* include *Corynebacterium glutamicum*, *Corynebacterium efficiens*, *Corynebacterium ammoniagenes*, *Corynebacterium halotolerance*, and *Corynebacterium alkanolyticum*. Among them, *Corynebacterium glutamicum* is preferred for safety and high 4-HBA production. Examples of preferred strains include *Corynebacterium glutamicum* R (FERM BP-18976), ATCC13032, ATCC13869, ATCC13058, ATCC13053, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). These strains are deposited internationally under the Budapest Treaty and available to the public. Among them, strains R (FERM BP-18976), ATCC13032, and ATCC13869 are preferred.

According to molecular biological classification, names of some species of coryneform bacteria, such as *Brevibacterium flavum*, *Brevibacterium lactofermentum*, *Brevibacterium divaricatum*, and *Corynebacterium lilium* are standardized to *Corynebacterium glutamicum* (Liebl, W. et al., Transfer of *Brevibacterium divaricatum* DSM 20297T, "*Brevibacterium Flavum*" DSM 20411, "*Brevibacterium*

*lactofermentum*" DSM 20412 and DSM 1412, and *Corynebacterium glutamicum* and their distinction by rRNA gene restriction patterns. Int. J. Syst. Bacteriol. 41:255-260. (1991); and Kazuo Komagata et al., "Classification of the coryneform group of bacteria", Fermentation and industry, 45:944-963 (1987)).

Examples of the genus *Brevibacterium* include *Brevibacterium ammoniagenes* (for example, ATCC6872), Examples of the genus *Arthrobacter* include *Arthrobacter globiformis* (for example, ATCC8010, ATCC4336, ATCC21056, ATCC31250, ATCC31738 and ATCC35698).

Examples of the genus *Mycobacterium* include *Mycobacterium bovis* (for example, ATCC19210 and ATCC27289).

Examples of the genus *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IFO3764).

The coryneform bacteria may be, let alone a wild type, a mutant thereof or an artificial recombinant thereof. Examples thereof include disruptants in which a gene of lactate dehydrogenase, phosphoenolpyruvate carboxylase, or malate dehydrogenase is disrupted. Among them, preferred is a disruptant in which a lactate dehydrogenase gene is disrupted. In the disruptant, the lactate dehydrogenase gene is disrupted and the metabolic pathway from pyruvic acid to lactic acid, is blocked. Particularly preferred is a disruptant of *Corynebacterium glutamicum*, especially the R (FERM BP-18976) strain in which the lactate dehydrogenase gene is disrupted.

Such a disruptant can be prepared based on a conventional gene engineering process. Such a lactate dehydrogenase disruptant and the preparation process thereof are described in WO 2005/010182 A1, for example.

The inventors found that, as shown in FIG. 1, coryneform bacteria have extremely higher 4-HBA resistance compared with other bacteria. In this regard, coryneform bacteria are suitable for the 4-HBA production by the method of the present invention.

Chorismate-Pyruvate Lyase Gene

Chorismate-pyruvate lyase is an enzyme that catalyzes a reaction in which 4-HBA and pyruvic acid are produced from chorismic acid.

The gene which encodes an enzyme having chorismate-pyruvate lyase activity may be of any origin without particular limitation, and examples thereof include genes of microorganisms of the genus *Pantoea*, the genus *Providencia*, the genus *Escherichia*, the genus *Pseudoalteromonas*, the genus *Cronobacter*, the genus *Citrobacter*, the genus *Enterobacter*, the genus *Pseudomonas*, the genus *Morganella*, the genus *Azotobacter*, the genus *Shewanella*, or the genus *Cupriavidus*.

For a higher enzyme specific activity, genes of the microorganisms of the genus *Pantoea*, the genus *Providencia*, the genus *Escherichia*, the genus *Pseudoalteromonas*, the genus *Cronobacter*, the genus *Citrobacter*, or the genus *Enterobacter* are preferred. For a higher resistance to the product, 4-HBA, genes of the microorganisms of the genus *Providencia*, the genus *Enterobacter*, the genus *Shewanella*, or the genus *Cupriavidus* are preferred. For a higher 4-HBA productivity of the transformant, genes of the microorganisms of the genus *Pantoea*, the genus *Providencia*, the genus *Escherichia*, or the genus *Cronobacter* are preferred. Comprehensively, genes of the genus *Providencia* or the genus *Cronobacter* are more preferred.

Specific examples of such genes include the genes of *Pantoea ananatis, Providencia rustigianii, Providencia stuartii, Providencia sneebia, Providencia rettgeri, Providencia alcalifaciens, Providencia burhodogranariea, Escherichia coli, Escherichia fergusonii, Pseudoalteromonas piscicida, Pseudoalteromonas haloplanktis, Cronobacter sakazakii, Citrobacter youngae, Citrobacter koseri, Enterobacter aerogenes, Enterobacter cloacae, Pseudomonas putida, Morganella morganii, Azotobacter vinelandii, Shewanella putrefaciens*, and *Cupriavidus taiwanensis*.

Examples of the gene of *Pantoea ananatis* include the gene consisting of the base sequence of SEQ ID NO: 1, examples of the gene of *Providencia rustigianii* include the gene consisting of the base sequence of SEQ ID NO: 2, examples of the gene of *Providencia stuartii* include the gene consisting of the base sequence of SEQ ID NO: 3, examples of the gene of *Providencia sneebia* include the gene consisting of the base sequence of SEQ ID NO: 4, examples of the gene of *Providencia rettgeri* include the gene consisting of the base sequence of SEQ ID NO: 5, examples of the gene of *Providencia alcalifaciens* include the gene consisting of the base sequence of SEQ ID NO: 6, examples of the gene of *Providencia burhodogranariea* include the gene consisting of the base sequence of SEQ ID NO: 7, examples of the gene of *Escherichia coli* include the gene consisting of the base sequence of SEQ ID NO: 3, examples of the gene of *Escherichia fergusonii* include the gene consisting of the base sequence of SEQ ID NO: 9, examples of the gene of *Pseudoalteromonas piscicida* include the gene consisting of the base sequence of SEQ ID NO: 10, examples of the gene of *Pseudoalteromonas haloplanktis* include the gene consisting of the base sequence of SEQ ID NO: 11, examples of the gene of *Cronobacter sakazakii* include the gene consisting of the base sequence of SEQ ID NO: 12, examples of the gene of *Citrobacter youngae* include the gene consisting of the base sequence of SEQ ID NO: 13, examples of the gene of *Citrobacter koseri* include the gene consisting of the base sequence of SEQ ID NO: 14, examples of the gene of *Enterobacter aerogenes* include the gene consisting of the base sequence of SEQ ID NO: 15, examples of the gene of *Enterobacter cloacae* include the gene consisting of the base sequence of SEQ ID NO: 16, examples of the gene of *Pseudomonas putida* include the gene consisting of the base sequence of SEQ ID NO: 17, examples of the gene of *Morganella morganii* include the gene consisting of the base sequence of SEQ ID NO: 18, examples of the gene of *Azotobacter vinelandii* include the gene consisting of the base sequence of SEQ ID NO: 19, examples of the gene of *Shewanella putrefaciens* include the gene consisting of the base sequence of SEQ ID NO: 20, and examples of the gene of *Cupriavidus taiwanensis* include the gene consisting of the base sequence of SEQ ID NO: 21.

Also, a DNA (analog) which hybridizes to a DNA consisting of a complementary base sequence of any one of SEQ ID NOs: 1 to 21 under stringent conditions and which encodes a polypeptide having chorismate-pyruvate lyase activity can be used. In the present invention, "stringent conditions" means conditions in which hybridization is performed in a hybridization solution at a salt concentration of 6×SSC at 50 to 60° C. for 16 hours and then washing with a solution at 0.1×SSC is performed.

Also, a DNA (analog) which hybridizes to a DNA consisting of a base sequence having 90% or more, in particular 95% or more, in particular 98% or more, of homology with any one of SEQ ID NOs: 1 to 21 and which encodes a polypeptide having chorismate-pyruvate lyase activity can be used.

In the present invention, the base sequence homology was calculated using GENETYX Ver. 8 (made by Genetyx).

The chorismate-pyruvate lyase activity can be measured by an altered method of the method described in "Microbiology, 140, 897-904 (1994)". Briefly, the enzyme to be tested is added to a test solution containing 50 mM of Tris-HCl (pH 7.5), 0.5 mM of chorismate Ba salt, 0.2 mM of NADH, 0.2 M of NaCl and 5 units of lactate dehydrogenase, the reaction is allowed to proceed at 33° C., and the decrease in absorbance of NADH at 340 nm is monitored to determine the initial rate of the reaction. Using a system not containing the chorismate Ba salt, the reaction is performed in a similar manner to obtain background values. The difference between the measurements is considered to result from the chorismate-pyruvate lyase activity. When linear reduction in the absorbance of NADH at 340 nm with time is observed (which reduction depends on the enzyme and the substrate added), chorismate-pyruvate lyase activity is judged to exist. One unit of enzyme activity is defined as the amount of the enzyme that produces 1 μmol of 4-HBA per minute, and was calculated from the initial rate of the enzyme reaction.

The analog of the DNA consisting of a base sequence of any one of SEQ ID NOs: 1 to 21 can be selected from, for example, a DNA library of a different species by PCR or hybridization using a primer or a probe designed based on the base sequence, according to a conventional method, and as a result, a DNA which encodes a polypeptide having chorismate-pyruvate lyase activity can be obtained with a high probability.

Preferably, the transformant of the present invention does not have any 4-hydroxybenzoate decarboxylase gene introduced thereinto. 4-Hydroxybenzoate decarboxylase is an enzyme that converts 4-HBA into phenol. Since a coryneform bacterium does not have any endogenous 4-hydroxybenzoate decarboxylase gene, the coryneform bacterium does not perform the conversion from 4-HBA to phenol unless it has an exogenous 4-hydroxybenzoate decarboxylase gene introduced thereinto. In the cases where a 4-hydroxybenzoate decarboxylase gene, in addition to a chorismate-pyruvate lyase gene, is introduced, the transformant becomes capable of producing phenol from a sugar, such as glucose, via 4-HBA.

However, phenol generally inhibits enzymes much more strongly than 4-HBA does. Therefore, an attempt to produce phenol from a sugar through a multistep reaction results in poor production efficiency because phenol inhibits not a few kinds of enzymes. In contrast, in the cases where 4-HBA, which is less toxic, is produced from a sugar using a transformant not having any 4-hydroxybenzoate decarboxylase gene but having a chorismate-pyruvate lyase gene introduced thereinto, and then phenol is separately produced from the 4-HBA using a transformant having a 4-hydroxybenzoate decarboxylase gene introduced thereinto or using 4-hydroxybenzoate decarboxylase as an enzyme, the efficiency of the phenol production is relatively high because no other enzymes but 4-hydroxybenzoate decarboxylase is adversely affected by phenol.

In addition, phenol generally has a much stronger cytotoxicity as compared to 4-HBA. Producing phenol from a sugar using a microorganism takes a long time because the production goes through a multistep reaction. Therefore, the microorganism is exposed to the resulting phenol for a prolonged time, and is affected by the cytotoxicity, which leads to poor production efficiency. In contrast, in the cases where 4-HBA, which is less cytotoxic, is produced from a sugar using a transformant not having any 4-hydroxybenzoate decarboxylase gene but having a chorismate-pyruvate lyase gene introduced thereinto, the transformant is less damaged despite the lengthy multistep reaction. When phenol is separately produced from the 4-HBA using a transformant having a 4-hydroxybenzoate decarboxylase gene introduced thereinto or using 4-hydroxybenzoate decarboxylase as an enzyme, phenol can efficiently be produced from a sugar.

Construction of Vector for Transformant

The DNA which encodes chorismate-pyruvate lyase is amplified by PCR and then cloned into a suitable vector which is replicable in a host.

The plasmid vector may be any plasmid vector as long as it comprises a gene responsible for autonomously replicating function in a coryneform bacterium. Specific examples of the plasmid vector include pAM330 of *Brevibacterium lactofermentum* 2256 (JP 58-67696 A; Miwa, K. et al., Cryptic plasmids in glutamic acid-producing bacteria. Agric. Biol. Chem. 48: 2901-2903 (1984); and Yamaguchi, R. et al., Determination of the complete nucleotide sequence of the *Brevibacterium lactofermentum* plasmid pAM 330 and the analysis of its genetic information. Nucleic Acids Symp. Ser. 16: 265-267 (1985)), pHM1519 of *Corynebacterium glutamicum* ATCC3058 (Miwa, K. et al., Cryptic plasmids in glutamic acid-producing bacteria. Agric. Biol. Chem. 48:2901-2903 (1984)), pCRY30 of the same *Corynebacterium glutamicum* ATCC3058 (Kurusu, Y. et al., Identification of plasmid partition function in coryneform bacteria. Appl. Environ. Microbiol. 57: 759-764 (1991)), pCG4 of *Corynebacterium glutamicum* T250 (JP 57-183799 A; and Katsumata, R. et al., Protoplast transformation of glutamate-producing bacteria with plasmid DNA. J. Bacteriol., 159: 306-311 (1984)), pAG1, pAG3, pAG14, and pAG50 of the same *Corynebacterium glutamicum* T250 (JP 62-166890 A), pEK0, pEC5, and pEKEx1 of the same *Corynebacterium glutamicum* T250 (Eikmanns, B. J. et al., A family of *Corynebacterium glutamicum*/*Escherichia coli* shuttle vectors for cloning, controlled, gene expression, and promoter probing. Gene, 102: 33-98 (1991)), etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are of *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Among them, preferred for a coryneform bacterium is electroporation, which can be performed by a known method (Kurusu, Y. et al., Electroporation-transformation system for Coryneform bacteria by auxotrophic complementation, Agric. Biol. Chem. 54: 443-447 (1990)).

The transformant is cultured using a culture medium usually used for culture of microorganisms. The culture medium may be a natural medium or a synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. These carbon sources may be used singly or as a mixture of two or more kinds. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. These nitrogen sources may be used singly or as a mixture of two or more kinds. The concentration of these nitrogen sources in the culture medium varies depending on the kind of the nitrogen compound, but is usually 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used singly or as a mixture of two or more kinds. The concentration of the inorganic salts in the culture medium varies depending on the kind of the inorganic salts, but is usually about 0.1 to 1 w/v %.

Examples of the nutritional substances include, for example, meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium is usually about 0.1 to 10 w/v %. Further, vitamins may be added as needed. Examples of the vitamins include biotin, thiamine, pyridoxine, pantothenic acid, inositol, nicotinic acid, etc.

The pH of the culture medium is preferably about 6 to 8.

Preferable examples of the microbial culture medium include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

Disruption or Deletion in Host Chromosomal Gene

In the coryneform bacterium as a host, the 4-hydroxybenzoate hydroxylase gene on the chromosome preferably has a disruption or deletion. Due to the disruption of 4-hydroxybenzoate hydroxylase, the metabolism of 4-HBA produced is inhibited, resulting in an improved 4-HBA productivity and reduced by-products.

Replacement: of a gene on the chromosome with the corresponding gene having a disruption or deletion can be achieved by creating a gene with deletion mutation for not producing a normally functioning enzyme protein, and transforming a bacterium with a DNA comprising the mutated gene for homologous recombination between the gene on the chromosome and the mutated gene. An enzyme protein encoded by a gene having a disruption or deletion, even when produced, has a conformation different from that of the wild type, and has no or reduced function. The gene deletion or gene disruption by way of gene substitution through the use of homologous recombination has already been established, and examples thereof include a method using a plasmid containing a temperature sensitive replication origin or a plasmid capable of conjugal transfer, and a method using a suicide vector not having a replication origin in a host (U.S. Pat. No. 6,303,383, JP 05-007491 A).

(2) Process for Producing 4-HBA

4-HBA can be produced by a method comprising a step of reacting the transformant of the present invention described above in a reaction mixture containing at least one starting compound selected from the group consisting of a sugar, a compound from which the transformant is capable of producing chorismic acid by metabolism, and chorismic acid, and a salt thereof, and a step of recovering 4-HBA from the reaction mixture.

The starting compound must be a compound that can be taken into the transformant and that is easily available for industrial applications, i.e., one abundantly present in plants, for example.

Glucose is preferred as the sugar, but other sugars capable of being metabolized into glucose can also be used. Such sugars include oligosaccharides and polysaccharides that have a glucose unit. Examples of such sugars include monosaccharides, such as fructose, mannose, arabinose, xylose, and galactose; disaccharides, such as cellobiose, sucrose, lactose, maltose, trehalose, cellobiose, and xylobiose; polysaccharides, such as dextrin and soluble starch; etc.

Examples of the compound that can be metabolized into chorismic acid include quinic acid, shikimic acid, and the like.

Also, molasses, which contains these starting compounds, can also be used, for example. In addition, a saccharified solution which is obtainable by saccharifying, using a diastatic enzyme, non-edible agricultural waste including straw (rice straw, barley straw, wheat straw, rye straw, oat straw, etc.), bagasse, and corn stover; energy crops including switchgrass, napier grass, and Miscanthus; wood waste; waste paper; etc. and which contains two or more kinds of sugars, including glucose, can also be used. Among the above-mentioned starting compounds, glucose, chorismic acid, quinic acid, and shikimic acid are preferred.

Growth of Microorganism

Before the reaction, the transformant is preferably cultured and grown under aerobic conditions at about 25 to 38° C. for about 12 to 48 hours.

Culture Medium

The culture medium used for aerobic culture of the transformant before the reaction may be a natural medium or a synthetic medium containing a carbon source, a nitrogen source, inorganic salts, other nutritional substances, etc.

Examples of the carbon source that can be used include sugars (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used singly or as a mixture of two or more kinds.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. These nitrogen sources may be used singly or as a mixture of two or more kinds. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used singly or as a mixture of two or more kinds. The concentration of the inorganic salts in the culture medium varies depending on the kind of the inorganic salts, but is usually about 0.01 to 1 w/v %.

Examples of the nutritional substances include meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a sugar at a concentration in the above-mentioned range.

Reaction Mixture

The reaction mixture may be a natural or synthetic reaction mixture containing a carbon source, a nitrogen source, inorganic salts, other nutritional substances, etc.

The carbon source may be one or more of the above-described starting compounds, or a molasses or a saccharified solution containing such compounds. As the carbon source, besides sugars, sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin can also be used.

These carbon sources may be used singly or as a mixture of two or more kinds.

The concentration of the starting compound in the reaction mixture is preferably about 1 to 20 w/v %, more preferably about 2 to 10 w/v %, and still more preferably about 2 to 5 w/v %.

The total concentration of the carbon sources including the starting compound in the reaction mixture is usually about 2 to 5 w/v %.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. These nitrogen sources may be used singly or as a mixture of two or more kinds. The concentration of these nitrogen sources in the reaction mixture varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used singly or as a mixture of two or more kinds. The concentration of the inorganic salts in the reaction mixture varies depending on the kind of the inorganic salts, but is usually about 0.01 to 1 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the reaction mixture is preferably about 6 to 8.

Specific examples of the preferable reaction mixture for coryneform bacteria include the above-mentioned BT medium, etc. Such a culture medium can be used after prepared so as to contain a sugar at a concentration in the above-mentioned range.

Reaction Conditions

The reaction temperature, that is, the temperature for keeping the transformant alive during the reaction is preferably about 20 to 50° C., and more preferably about 25 to 47° C. When the temperature is in the above range, 4-HBA can be efficiently produced.

The reaction period is preferably about 1 to 7 days, and more preferably about 1 to 3 days.

The culture may be a batch process, a fed-batch process, or a continuous process. Among them, a batch process is preferred.

The reaction may be performed under aerobic conditions or reducing conditions. The 4-HBA production ability of the transformant of the present invention itself is higher under aerobic conditions. However, aerobic conditions favor the growth of the transformant and the starting compound is consumed for the growth. Accordingly, the 4-HBA production efficiency is lowered.

Therefore, it is preferred that the reaction is performed under aerobic conditions where the transformant does not grow. In the present invention, "does not grow" includes "substantially does not grow" and "hardly grows". For example, growth of the transformant can be avoided or inhibited by the use of a reaction mixture that has a deficiency or limitation in one or more of compounds essential for the growth of the microorganism, for example, vitamins, such as biotin and thiamine, nitrogen sources, etc.

Under reducing conditions, coryneform bacteria substantially do not grow, and therefore, the starting compound is not consumed for the growth, which leads to a higher 4-HBA production efficiency.

The "reducing conditions" is defined based on the oxidation-reduction potential of the reaction mixture. The oxidation-reduction potential of the reaction mixture is preferably about −200 mV to −500 mV, and more preferably about −150 mV to −500 mV.

The reducing conditions of the reaction mixture can be simply estimated using resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or *Nogeikagaku Jikkensho*, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

In the case of a reaction under reducing conditions, it is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Recovery of 4-HBA

Through the culture performed in the above manner, 4-HBA is produced in the reaction mixture. 4-HBA can be recovered by collecting the reaction mixture, and it is also feasible to isolate 4-HBA from the reaction mixture by a known method. Examples of such a known method include the ion-exchange resin method, the concentration method, the crystallization method, the membrane separation method, the organic solvent extraction method, various adsorption methods, etc.

EXAMPLES

Example 1

Cloning and Expression of 4-Hydroxy Benzoate-Producing Genes (Chorismate-Pyruvate Lyase Genes)

(1) Extraction of Chromosomal DNA from Microorganisms

To extract chromosomal DNA from *Pantoea ananatis* LMG 20103, the bacterium was inoculated into LMG Bacteria Culture Medium No. 1 (1 g of beef extract, 2 g of yeast extract, 5 g of peptone, and 5 g of NaCl were dissolved in 1 L of distilled water, and the pH was adjusted to 7.4) using a platinum loop, and cultured with shaking at 28° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Providencia rustigianii* (JCM 3953), the bacterium was inoculated into JCM Medium No. 12 (5 g of peptone, 3 g of beef extract, and 5 g of NaCl were dissolved in 1 L of distilled water, and the pH was adjusted to 7.0) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Providencia stuartii* (ATCC 25827), the bacterium was inoculated into ATCC Medium No. 3 (5 g of peptone and 3 g of beef extract were dissolved in 1 L of distilled water, and the pH was adjusted to 6.8) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Providencia sneebia* (JCM 16941), the bacterium was inoculated into JCM Medium No. 27 (15 g of peptone, 5 g of soya peptone, and 5 g of NaCl were dissolved in 1 L of distilled water) using a platinum loop, and cultured with shaking at 28° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Providencia rettgeri* (JCM 1675), the bacterium was inoculated into JCM Medium No. 12 (5 g of peptone, 3 g of beef extract, and 5 g of NaCl were dissolved in 1 L of distilled water, and the pH was adjusted to 7.0) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Providencia alcalifaciens* (JCM 1673), the bacterium was inoculated into JCM Medium No. 12 (5 g of peptone, 3 g of beef extract, and 5 g of NaCl were dissolved in 1 L of distilled water, and the pH was adjusted to 7.0) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Providencia burhodograniea* (JCM 16940), the bacterium was inoculated into JCM Medium No. 21 (15 g of peptone, 5 g of soya peptone, and 5 g of NaCl were dissolved in 1 L of distilled water) using a platinum loop, and cultured with shaking at 28° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Escherichia coli* (K12 MG1655), the bacterium was inoculated into LB Medium (10 g of tryptone, 5 g of yeast extract, and 5 g of NaCl were dissolved in 1 L of distilled water) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Escherichia fergusonii* NBRC102419, the bacterium was inoculated into NBRC Medium No. 802 (10 g of polypeptone, 2 g of yeast extract, and 1 g of $MgSO_4.7H_2O$ were dissolved in 1 L of distilled water, and the pH was adjusted to 7.0) using a platinum loop, and cultured with shaking at 30° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Pseudoalteromonas piscicida* (JCM 20779), the bacterium was inoculated into JCM Medium No. 118 (37.4 g of Marine Broth 2216 (made by Becton, Dickinson and Company) was dissolved in 1 L of distilled water) using a platinum loop, and cultured with shaking at 30° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Pseudoalteromonas haloplanktis* (NBRC 102225), the bacterium was inoculated into NBRC Medium No. 304 (37.4 g of Marine Broth 2216 (made by Becton, Dickinson and Company) was dissolved in 1 L of distilled water) using a platinum loop, and cultured with shaking at 25° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Cronobacter sakazakii* (JCM 1233), the bacterium was inoculated into JCM Medium No. 12 (5 g of peptone, 3 g of beef extract, and 5 g of NaCl were dissolved in 1 L of distilled water, and the pH was adjusted to 7.0) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Citrobacter youngae* (ATCC 29220), the bacterium was inoculated into ATCC Medium No. 3 (5 g of peptone and 3 g of beef extract were dissolved in 1 L of distilled water, and the pH was adjusted to 6.8) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Citrobacter koseri* (ATCC BAA-395), the bacterium was inoculated into ATCC Medium Mo. 18 (15 g of peptone, 5 g of soya peptone, and 5 g of NaCl were dissolved in 1 L of distilled water) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Enterobacter aerogenes* NBRC 13534, the bacterium was inoculated into NBRC Medium No. 802 (10 g of polypeptone, 2 g of yeast extract, and 1 g of $MgSO_4.7H_2O$ were dissolved in 1 L of distilled water, and the pH was adjusted to 7.0) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Enterobacter cloacae* NBRC 13535, the bacterium was inoculated into NBRC Medium No. 802 (10 g of polypeptone, 2 g of yeast extract, and 1 g of $MgSO_4.7H_2O$ were dissolved in 1 L of distilled water, and the pH was adjusted to 7.0) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Pseudomonas putida* (ATCC 47054), the bacterium was inoculated into ATCC Medium No. 1065 (10 g of tryptone, 5 g of yeast extract, and 5 g of NaCl were dissolved in 1 L of distilled water) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual, To extract chromosomal DNA from *Morganella morganii* NBRC 3848, the bacterium was inoculated into NBRC Medium No. 802 (10 g of polypeptone, 2 g of yeast extract, and 1 g of $MgSO_4.7H_2O$ were dissolved in 1 L of distilled water, and the pH was adjusted to 7.0) using a platinum loop, and cultured with shaking at 30° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Azotobacter vinelandii* (ATCC 9104), the bacterium was inoculated into NBRC Medium No. 805 (1 g of east extract, 5 g of mannitol, 0.7 g of $K_2HPO_4$, 0.1 g of $KH_2PO_4$, and 1 g of $MgSO_4 \cdot 7H_2O$ were dissolved in 1 L of distilled water, and the pH was adjusted to 7.0-7.2) using a platinum loop, and cultured with shaking at 26° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Shewanella putrefaciens* (JCM 20190), the bacterium was inoculated into JCM Medium No. 22 (10 g of peptone, 10 g of beef extract, and 5 g of NaCl were dissolved in 1 L of distilled water, and the pH was adjusted to 7.0-7.2) using a platinum loop, and cultured with shaking at 25° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Cupriavidus taiwanensis* (LMG 19424), the bacterium was inoculated into JCM Medium No. 27 (15 g of peptone, 5 g of soya peptone, and 5 g of NaCl were dissolved in 1 L of distilled water) using a platinum loop, and cultured with shaking at 25° C. until the logarithmic growth phase After the bacterial cells were collected, chromosomal DNA was recovered from the collected cells using a DNA extraction kit (trade name: GenomicPrep Cells and Tissue DNA Isolation Kit, made by Amersham) according to the instruction manual.

(2) Cloning of 4-Hydroxy Benzoate-Producing Genes (Chorismate-Pyruvate Lyase Genes)

A DNA fragment comprising the ubiC gene which encodes a 4-hydroxy benzoate-producing gene (chorismate-pyruvate lyase gene) was amplified by the PCR method as described below.

In the PCR, the sets of primers shown below were synthesized based on SEQ ID NO: 1 (*Pantoea ananatis* ubiC gene), SEQ ID NO: 2 (*Providencia rustigianii* ubiC gene), SEQ ID NO: 3 (*Providencia stuartii* ubiC gene), SEQ ID NO: 4 (*Providencia sneebia* ubiC gene), SEQ ID NO: 5 (*Providencia rettgeri* ubiC gene), SEQ ID NO: 6 (*Providencia alcalifaciens* ubiC gene), SEQ ID NO: 7 (*Providencia burhodogranariea* ubiC gene), SEQ ID NO: 3 (*Escherichia coli* ubiC gene), SEQ ID NO: 9 (*Escherichia fergusonii* ubiC gene), SEQ ID NO: 10 (*Pseudoalteromonas piscicida* ubiC gene), SEQ ID NO: 11 (*Pseudoalteromonas haloplanktis* ubiC gene), SEQ ID NO: 12 (*Cronobacter sakazakii* ubiC gene), SEQ ID NO: 13 (*Citrobacter youngae* ubiC gene), SEQ ID NO: 14 (*Citrobacter koseri* ubiC gene), SEQ ID NO: 15 (*Enterobacter aerogenes* ubiC gene), SEQ ID NO: 16 (*Enterobacter cloacae* ubiC gene), SEQ ID NO: 17 (*Pseudomonas putida* ubiC gene), SEQ ID NO: 18 (*Morganella morganii* ubiC gene), SEQ ID NO: 19 (*Azotobacter vinelandii* ubiC gene), SEQ ID NO: 20 (*Shewanella putrefaciens* ubiC gene), and SEQ ID NO: 21 (*Cupriavidus taiwanensis* ubiC gene), and used for cloning of the corresponding ubiC gene.

```
Primers for Pantoea ananatis ubiC gene
amplification
(a-1);
                                      (SEQ ID NO: 22)
5'-CTCTCATATGACGCAAGACCCGCT-3'

(b-1);
                                      (SEQ ID NO: 23)
5'-CTCTCATATGTTAACCTTGATCACGATAGAGCG-3'
```

Primers (a-1) and (b-1) each have an NdeI restriction enzyme site added thereto.

```
Primers for Providencia rustigianii ubiC gene
amplification
(a-2);
                                      (SEQ ID NO: 24)
5'-CTCTCATATGCATGAAACAATTTTTACCCATCATCC-3'

(b-2);
                                      (SEQ ID NO: 25)
5'-CTCTCATATGGATTATGTTAGATAGTTATCTATATGCAGGTG-3'
```

Primers (a-2) and (b-2) each have an NdeI restriction enzyme site added thereto.

```
Primers for Providencia stuartii ubiC gene
amplification
(a-3);
                                      (SEQ ID NO: 26)
5'-CTCTCATATGGATGAAACGCTTTTTATCTCTCAC-3'

(b-3);
                                      (SEQ ID NO: 27)
5'-CTCTCATATGTCCCTCCATTTGTTGTGCTC-3'
```

Primers (a-3) and (b-3) each have an NdeI restriction enzyme site added thereto.

```
Primers for Providencia sneebia ubiC gene
amplification
(a-4);
                                      (SEQ ID NO: 28)
5'-CTCTCATATGGATGATACGCTTTTTACCTCTC-3'

(b-4);
                                      (SEQ ID NO: 29)
5'-CTCTCATATGCTTCCCTTCACTTGTCATGC-3'
```

Primers (a-4) and (b-4) each have an NdeI restriction enzyme site added thereto.

```
Primers for Providencia rettgeri ubiC gene
amplification
(a-5);
                                      (SEQ ID NO: 30)
5'-CTCTCATATGGATGAAACGCTTTTTACTTCTCAG-3'

(b-5);
                                      (SEQ ID NO: 31)
5'-CTCTCATATGTTAACGATATGCAGGTGATTCAGG-3'
```

Primers (a-5) and (b-5) each have an NdeI restriction enzyme site added thereto.

```
Primers for Providencia alcalifaciens ubiC gene
amplification
(a-6);
                                      (SEQ ID NO: 32)
5'-CTCTCATATGCATGAAACGATTTTTACCTCTCATC-3'

(b-6);
                                      (SEQ ID NO: 33)
5'-CTCTCATATGGTTATCTATATGCAGGTGATTCAGG-3'
```

Primers (a-6) and (b-6) each have an NdeI restriction enzyme site added thereto.

Primers for *Providencia burhodogranariea* ubiC gene amplification:
(a-7);
(SEQ ID NO: 34)
5'-CTCTCATATGGATGAAACGCTTTTTACCTCTC-3'

(b-7);
(SEQ ID NO: 35)
5'-CTCTCATATGATACTTCCCTCCACTTGTCG-3'

Primers (a-7) and (b-7) each have an NdeI restriction enzyme site added thereto.

Primers for *Escherichia coli* ubiC gene amplification
(a-8);
(SEQ ID NO: 36)
5'-CTCTCATATGTCACACCCCGCGTTAA-3'

(b-8);
(SEQ ID NO: 37)
5'-CTCTCATATGTTAGTACAACGGTGACGCC-3'

Primers (a-8) and (b-8) each have an NdeI restriction enzyme site added thereto.

Primers for *Escherichia fergusonii* ubiC gene amplification
(a-9);
(SEQ ID NO: 38)
5'-CTCTCATATGCTGATTTTGCAACAACTGGTG-3'

(b-9);
(SEQ ID NO: 39)
5'-CTCTCATATGTTAGTACAACGGTGATGCAGG-3'

Primers (a-9) and (b-9) each have an NdeI restriction enzyme site added thereto.

Primers for *Pseudoalteromonas piscicida* ubiC gene amplification
(a-10);
(SEQ ID NO: 40)
5'-CTCTCATATGCCTTTGCAATTACCCTTAGAG-3'

(b-10);
(SEQ ID NO: 41)
5'-CTCTCATATGAAGCCTGCCATTTCTGGTGG-3'

Primers (a-410) and (b-10) each have an NdeI restriction enzyme site added thereto.

Primers for *pseudoalteromonas haloplanktis* ubiC gene amplification
(a-11);
(SEQ ID NO: 42)
5'-CTCTCATATGATTACTTTCCCTGTTTCATTATCTGC-3'

(b-11);
(SEQ ID NO: 43)
5'-CTCTCATATGTCATGAGTACAAATACGCTCCTG-3'

Primers (a-11) and (b-11) each have an NdeI restriction enzyme site added thereto.

Primers for *Cronobacter sakazakii* ubiC gene amplification
(a-12);
(SEQ ID NO: 44)
5'-CTCTCATATGTCCCATCCCGCGCTGAG-3'

(b-12);
(SEQ ID NO: 45)
5'-CTCTCATATGTATTCTGCGTCAGGCTCCAC-3'

Primers (a-12) and (b-12) each have an NdeI restriction enzyme site added thereto.

Primers for *Citrobacter youngae* ubiC gene amplification
(a-13);
(SEQ ID NO: 46)
5'-CTCTCATATGCCACACCCTGCGTTAA-3'

(b-13);
(SEQ ID NO: 47)
5'-CTCTCATATGTCAGTACAACGGCGATGCA-3'

Primers (a-13) and (b-13) each have an NdeI restriction enzyme site added thereto.

Primers for *Citrobacter koseri* ubiC gene amplification
(a-14);
(SEQ ID NO: 48)
5'-CTCTCATATGTCACACCCTGCGTTAAG-3'

(b-14);
(SEQ ID NO: 49)
5'-CTCTCATATGTTAATACAACGGTGATGCGGG-3'

Primers (a-14) and (b-14) each have an NdeI restriction enzyme site added thereto.

Primers for *Enterobacter aerogenes* ubiC gene amplification
(a-15);
(SEQ ID NO: 50)
5'-CTCTCATATGCCACATCCTGCGCTTAC-3'

(b-15);
(SEQ ID NO: 51)
5'-CTCTCATATGTTAATACAATGGCGATGCAGGC-3'

Primers (a-15) and (b-15) each have an NdeI restriction enzyme site added thereto.

Primers for *Enterobacter cloacae* ubiC gene amplification
(a-16);
(SEQ ID NO: 52)
5'-CTCTCATATGTCACACCCTGCGGTAA-3'

(b-16);
(SEQ ID NO: 53)
5'-CTCTCATATGTCAGTACAACGGCGATGC-3'

Primers (a-16) and (b-16) each have an NdeI restriction enzyme site added thereto.

Primers for *Pseudomonas putida* ubiC gene amplification
(a-17);
(SEQ ID NO: 54)
5'-CTCTCATATGTCGTACGAATCCCCG-3'

(b-17);
(SEQ ID NO: 55)
5'-CTCTCATATGTCAGCGGTTTTCCTCCTTG-3'

Primers (a-17) and (b-17) each have an NdeI restriction enzyme site added thereto.

Primers for *Morganella morganii* ubiC gene amplification
(a-18);
(SEQ ID NO: 56)
5'-CTCTCATATGACACAAACAGTGATAACACCC-3'

(b-18);
(SEQ ID NO: 57)
5'-CTCTCATATGCCACGTTATTCTTCTCCGAG-3'

Primers (a-18) and (b-18) each have an NdeI restriction enzyme site added thereto.

Primers for *Azotobacter vinelandii* ubiC gene amplification
(a-19);
(SEQ ID NO: 58)
5'-CTCTCATATGACCGCTGCTCCCG-3'

(b-19);
(SEQ ID NO: 59)
5'-CTCTCATATGTTATAGGGTGTCCGGGTC-3'

Primers (a-19) and (b-19) each have an NdeI restriction enzyme site added thereto.

Primers for *Shewanella putrefaciens* ubiC gene amplification
(a-20);
(SEQ ID NO: 60)
5'-CTCTCATATGAATGTGACTAGCTTAAGCTTCC-3'

(b-20);
(SEQ ID NO: 61)
5'-CTCTCATATGTCACTGGCAAATTGCTCGC-3'

Primers (a-20) and (b-20) each have an NdeI restriction enzyme site added thereto.

Primers for *Cupriavidus taiwanensis* ubiC gene amplification
(a-21);
(SEQ ID NO: 62)
5'-CTCTCATATGAGCGCGCAGTCCGTG-3'

(b-21);
(SEQ ID NO: 63)
5'-CTCTCATATGCAGTTTCATCTCGTGGTCTC-3'

Primers (a-21) and (b-21) each have an NdeI restriction enzyme site added thereto.

As the template DNA, chromosomal DNAs extracted from *Pantoea ananatis* LMG 20103, *Providencia rustigianii* JCM 3953, *Providencia stuartii* ATCC 25827, *Providencia sneebia* JCM 16941, *Providencia rettgeri* JCM 1675, *Providencia alcalifaciens* JCM 1673, *Providencia burhodogranariea* JCM 16940, *Escherichia coli* MG1655, *Escherichia fergusonii* NBRC 102419, *Pseudoalteromonas piscicida* JCM 2C-779, *Pseudoalteromonas haloplanktis* NBRC 102225, *Cronobacter sakazakii* JCM 1233, *Citrobacter youngae* ATCC 29220, *Citrobacter koseri* ATCC BAA-395, *Enterobacter aerogenes* NBRC 13534, *Enterobacter cloacae* NBRC 13535, *Pseudomonas putida* ATCC 47054, *Morganella morganii* NBRC 3848, *Azotobacter vinelandii* ATCC 9104, *Shewanella putrefaciens* JCM 20190, and *Cupriavidus taiwanensis* LMG 1942 were used.
*) Abbreviations of the institutes from which the strains were purchased stand for the following.
<Organization Abbreviations>
ATCC: American Type Culture Collection
JCM: Japan Collection of Microorganisms
LMG: Belgian Co-ordinated Collections of Micro-organisms/Laboratory for Microbiology of the Faculty of Sciences of Ghent University (BCCM/LMG)
NBRC: NITE Biological Resource Center Actual PCR was performed using a Veriti thermal cycler (made by Applied Biosystems) and PrimeSTAR GXL DNA Polymerase (made by Takara Bio, Inc.) as a reaction reagent under the conditions described below.
Reaction Mixture:

| | |
|---|---|
| PrimeSTAR GXL DNA Polymerase (1.25 U/µL) | 1 µL |
| 5× PrimeSTAR GXL Buffer (Mg2+ plus) | 10 µL |
| dNTP Mixture (2.5 mM each) | 4 µL |
| Template DNA | 1 µL (DNA content: 1 µg or less) |
| The above 2 primers*) | 1 µL each (final conc.: 0.2 µM) |
| Sterile distilled water | 32 µL |

The above ingredients were mixed, and 50 µL of the reaction mixture was subjected to PCR.
*) For amplification of the ubiC gene of *Pantoea ananatis*, a combination of primers (a-1) and (b-1); for amplification of the ubiC gene of *Providencia rustigianii*, a combination of primers (a-2) and (b-2); for amplification of the ubiC gene of *Providencia stuartii*, a combination of primers (a-3) and (b-3); for amplification of the ubiC gene of *Providencia sneebia*, a combination of primers (a-4) and (b-4); for amplification of the ubiC gene of *Providencia rettgeri*, a combination of primers (a-5) and (b-5); for amplification of the ubiC gene of *Providencia alcalifaciens*, a combination of primers (a-6) and (b-6); for amplification of the ubiC gene of *Providencia burhodogranariea*, a combination of primers (a-7) and (b-7); for amplification of the ubiC gene of *Escherichia coli*, a combination of primers (a-8) and (b-8); for amplification of the ubiC gene of *Escherichia fergusonii*, a combination of primers (a-9) and (b-9); for amplification of the ubiC gene of *Pseudoalteromonas piscicida*, a combination of primers (a-10) and (b-10); for amplification of the ubiC gene of *Pseudoalteromonas haloplanktis*, a combination of primers (a-11) and (b-11); for amplification of the ubiC gene of *Cronobacter sakazakii*, a combination of primers (a-12) and (b-12); for amplification of the ubiC gene of *Citrobacter youngae*, a combination of primers (a-13) and (b-13); for amplification of the ubiC gene of *Citrobacter koseri*, a combination of primers (a-14) and (b-14); for amplification of the ubiC gene of *Enterobacter aerogenes*, a combination of primers (a-15) and (b-15); for amplification of the ubiC gene of *Enterobacter cloacae*, a combination of primers (a-16) and (b-16); for amplification of the ubiC gene of *Pseudomonas putida*, a combination of primers (a-17) and (b-17); for amplification of the ubiC gene of *Morganella morganii*, a combination of primers (a-18) and (b-18); for amplification of the ubiC gene of *Azotobacter vinelandii*, a combination of primers (a-19) and (b-19); for amplification of the ubiC gene of *Shewanella putrefaciens*, a combination of primers (a-20) and (b-20); and for amplification of the ubiC gene of *Cupriavidus taiwanensis*, a combination of primers (a-21) and (b-21) were used.
PCR cycle:
Denaturation step: 98° C., 10 seconds
Annealing step: 50° C., 5 seconds
Extension step: 68° C.
*Pantoea ananatis* ubiC gene, 31 seconds
*Providencia rustigianii* ubiC gene, 31 seconds

*Providencia stuartii* ubiC gene, 32 seconds
*Providencia sneebia* ubiC gene, 32 seconds
*Providencia rettgeri* ubiC gene, 30 seconds
*Providencia alcalifaciens* ubiC gene, 30 seconds
*Providencia burhodogranariea* ubiC gene, 33 seconds
*Escherichia coli* ubiC gene, 30 seconds
*Escherichia fergusonii* ubiC gene, 40 seconds
*Pseudoalteromonas piscicida* ubiC gene, 33 seconds
*Pseudoalteromonas haloplanktis* ubiC gene, 33 seconds
*Cronobacter sakazakii* ubiC gene, 32 seconds
*Citrobacter youngae* ubiC gene, 30 seconds
*Citrobacter koseri* ubiC gene, 30 seconds
*Enterobacter aerogenes* ubiC gene, 30 seconds
*Enterobacter cloacae* ubiC gene, 30 seconds
*Pseudomonas putida* ubiC gene, 33 seconds
*Morganella morganii* ubiC gene, 32 seconds
*Azotobacter vinelandii* ubiC gene, 33 seconds
*Shewanella putrefaciens* ubiC gene, 34 seconds
*Cupriavidus taiwanensis* ubiC gene, 40 seconds A cycle consisting of the above 3 steps was repeated 30 times.

Using 10 µL of the above-produced reaction mixture, 0.8% agarose gel electrophoresis was performed. As a result, detected were an about 0.5-kb DNA fragment in the case of the ubiC gene of *Pantoea ananatis*, an about 0.5-kb DNA fragment in the case of the ubiC gene of *Providencia rustigianii*, an about 0.5-kb DNA fragment in the case of the ubiC gene of *Providencia stuartii*, an about 0.5-kb DNA fragment in the case of the ubiC gene of *Providencia sneebia*, an about 0.5-kb DNA fragment in the case of the ubiC gene of *Providencia rettgeri*, an about 0.5-kb DNA fragment in the case of the ubiC gene of *Providencia alcalifaciens*, an about 0.5-kb DNA fragment in the case of the ubiC gene of *Providencia burhodogranariea*, an about 0.5-kb DNA fragment in the case of the ubiC gene of *Escherichia coli*, an about 0.7-kb DNA fragment in the case of the ubiC gene of *Escherichia fergusonii*, an about 0.6-kb DNA fragment in the case of the ubiC gene of *Pseudoalteromonas piscicida*, an about 0.5-kb DNA fragment in the case of the ubiC gene of *Pseudoalteromonas haloplanktis*, an about 0.6-kb DNA fragment in the case of the ubiC gene of *Cronobacter sakazakii*, an about 0.5-kb DNA fragment in the case of the ubiC gene of *Citrobacter youngae*, an about 0.5-kb DNA fragment in the case of the ubiC gene of *Citrobacter koseri*, an about 0.5-kb DNA fragment in the case of the ubiC gene of *Enterobacter aerogenes*, an about 0.5-kb DNA fragment in the case of the ubiC gene of *Enterobacter cloacae*, an about 0.6-kb DNA fragment in the case of the ubiC gene of *Pseudomonas putida*, an about 0.5-kb DNA fragment in the case of the ubiC gene of *Morganella morganii*, an about 0.6-kb DNA fragment in the case of the ubiC gene of *Azotobacter vinelandii*, an about 0.6-kb DNA fragment in the case of the ubiC gene of *Shewanella putrefaciens*, and an about 0.7-kb DNA fragment in the case of the ubiC gene of *Cupriavidus taiwanensis*. Each DNA fragment was purified using NucleoSpin Gel and PCR Clean-Up (made by Takara Bio, Inc.).

(3) Construction of 4-Hydroxy Benzoate-Producing Gene (Chorismate-Pyruvate Lyase Gene) Expression Plasmids 10 µL of the about 0.5-kb DNA fragment comprising the ubiC gene of *Pantoea ananatis*, the about 0.5-kb DNA fragment comprising the ubiC gene of *Providencia rustigianii*, the about 0.5-kb DNA fragment comprising the ubiC gene of *Providencia stuartii*, the about 0.5-kb DNA fragment comprising the ubiC gene of *Providencia sneebia*, the about 0.5-kb DNA fragment comprising the ubiC gene of *Providencia rettgeri*, the about 0.5-kb DNA fragment comprising the ubiC gene of *Providencia alcalifaciens*, the about 0.5-kb DNA fragment comprising the ubiC gene of *Providencia burhodogranariea*, the about 0.5-kb DNA fragment comprising the ubiC gene of *Escherichia coli*, the about 0.7-kb DNA fragment comprising the ubiC gene of *Escherichia fergusonii*, the about 0.6-kb DNA fragment comprising the ubiC gene of *Pseudoalteromonas piscicida*, the about 0.5-kb DNA fragment comprising the ubiC gene of *Pseudoalteromonas haloplanktis*, the about 0.6-kb DNA fragment, comprising the ubiC gene of *Cronobacter sakazakii*, the about 0.5-kb DNA fragment comprising the ubiC gene of *Citrobacter youngae*, the about 0.5-kb DNA fragment comprising the ubiC gene of *Citrobacter koseri*, the about 0.5-kb DNA fragment comprising the ubiC gene of *Enterobacter aerogenes*, the about 0.5-kb DNA fragment comprising the ubiC gene of *Enterobacter cloacae*, the about 0.6-kb DNA fragment comprising the ubiC gene of *Pseudomonas putida*, the about 0.5-kb DNA fragment comprising the ubiC gene of *Morganella morganii*, the about 0.6-kb DNA fragment comprising the ubiC gene of *Azotobacter vinelandii*, the about 0.6-kb DNA fragment comprising the ubiC gene of *Shewanella putrefaciens*, or the about 0.7-kb DNA fragment comprising the ubiC gene of *Cupriavidus taiwanensis*, each of which was amplified by the PCR in the above (2), and 2 of the cloning vector pCRB209 comprising a promoter PgapA (WO 2012/033112) were each cut using the restriction enzyme NdeI and processed at 70° C. for 10 minutes for deactivation of the restriction enzyme Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. The resulting liquid was named Ligation Liquids A, B, C, D, E, F, G, H, I, J, K, L, M, N, O, P, Q, R, S, T, or U.)

Using the obtained 21 kinds of Ligation Liquids A, B, C, D, E, F, G, H, I, J, K, L, M, N, O, P, Q, R, S, T, and U separately, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut using the restriction enzyme to confirm the inserted fragment. As a result, in addition to an about 5.1-kb DNA fragment of the plasmid pCRB209, confirmed were an about 0.5-kb inserted fragment in the case of the ubiC gene of *Pseudomonas putida* (Ligation Liquid A), an about 0.5-kb inserted fragment in the case of the ubiC gene of *Providencia rustigianii* (Ligation Liquid B), an about 0.5-kb inserted fragment in the case of the ubiC gene of *Providencia stuartii* (Ligation Liquid C), an about 0.5-kb inserted fragment in the case of the ubiC gene of *Providencia sneebia* (Ligation Liquid D), an about 0.5-kb inserted fragment in the case of the ubiC gene of *Providencia rettgeri* (Ligation Liquid E), an about 0.5-kb inserted fragment in the case of the ubiC gene of *Providencia alcalifaciens* (Ligation Liquid F), an about 0.5-kb inserted fragment in the case of the ubiC gene of *Providencia burhodogranariea* (Ligation Liquid G), an about 0.5-kb inserted fragment in the case of the ubiC gene of *Escherichia coli* (Ligation Liquid H), an about 0.7-kb inserted fragment in the case of the ubiC gene of *Escherichia fergusonii* (Ligation Liquid I), an about 0.6-kb inserted fragment in the case of the ubiC gene of *Pseudoalteromonas piscicida* (Ligation Liquid J), an about 0.5-kb inserted fragment in the case of the ubiC gene of *Pseudoalteromonas haloplanktis* (Ligation Liquid K), an about 0.6-kb inserted fragment in the case of the ubiC gene of *Cronobacter sakazakii* (Ligation Liquid L), an about 0.5-kb inserted fragment in the case of the ubiC gene of *Citrobacter youngae* (Ligation Liquid M), an about 0.5-kb inserted fragment in the case of the ubiC gene of *Citrobacter koseri* (Ligation Liquid N), an about 0.5-kb inserted fragment in the case of the ubiC gene of *Enterobacter aerogenes* (Ligation Liquid P), an about 0.5-kb inserted fragment in the case of the ubiC gene of *Enterobacter cloacae* (Ligation Liquid P), an about 0.6-kb inserted fragment in the case of the ubiC gene of *Pseudomonas putida* (Ligation Liquid Q), an about 0.5-kb inserted fragment in the case of the ubiC gene of *Morganella morganii* (Ligation Liquid R), an about 0.6-kb inserted fragment in the case of the ubiC gene of *Azotobacter vinelandii* (Ligation Liquid S), an about 0.6-kb inserted fragment in the case of the ubiC gene of *Shewanella putrefaciens* (Ligation Liquid T), and an about 0.7-kb inserted fragment in the case of the ubiC gene of *Cupriavidus taiwanensis* (Ligation Liquid U).

The plasmid comprising the ubiC gene of *Pantoea ananatis* was named pHBA1, the plasmid comprising the ubiC gene of *Providencia rustigianii* was named pHBA2, the plasmid comprising the ubiC gene of *Providencia stuartii* was named pHBA3, the plasmid comprising the ubiC gene of *Providencia sneebia* was named pHBA4, the plasmid comprising the ubiC gene of *Providencia rettgeri* was named pHBA5, the plasmid comprising the ubiC gene of *Providencia alcalifaciens* was named pHBA6, the plasmid comprising the ubiC gene of *Providencia burhodogranariea* was named pHBA7, the plasmid comprising the ubiC gene of *Escherichia coli* was named pHBA8, the plasmid comprising the ubiC gene of *Escherichia fergusonii* was named pHBA9, the plasmid comprising the ubiC gene of *Pseudoalteromonas piscicida* was named pHBA10, the plasmid comprising the ubiC gene of *Pseudoalteromonas haloplanktis* was named pHBA11, the plasmid comprising the ubiC gene of *Cronobacter sakazakii* was named pHBA12, the plasmid comprising the ubiC gene of *Citrobacter youngae* was named pHBA13, the plasmid comprising the ubiC gene of *Citrobacter koseri* was named pHBA14, the plasmid comprising the ubiC gene of *Enterobacter aerogenes* was named pHBA15, the plasmid comprising the ubiC gene of *Enterobacter cloacae* was named pHBA16, the plasmid comprising the ubiC gene of *Pseudomonas putida* was named pHBA17, the plasmid comprising the ubiC gene of *Morganella morganii* was named pHBA18, the plasmid comprising the ubiC gene of *Azotobacter vinelandii* was named pHBA19, the plasmid comprising the ubiC gene of *Shewanella putrefaciens* was named pHBA20, and the plasmid comprising the ubiC gene of *Cupriavidus taiwanensis* was named pHBA21 (Table 1).

TABLE 1

4-Hydroxy benzoate producing-gene expression plasmid and origin of the gene

| Plasmid | Origin of 4-hydroxy benzoate producing gene |
| --- | --- |
| pHBA1 | *Pantoea ananatis* |
| pHBA2 | *Providencia rustigianii* |
| pHBA3 | *Providencia stuartii* |
| pHBA4 | *Providencia sneebia* |
| pHBA5 | *Providencia rettgeri* |
| pHBA6 | *Providencia alcalifaciens* |
| pHBA7 | *Providencia burhodogranariea* |
| pHBA8 | *Escherichia coli* |
| pHBA9 | *Escherichia fergusonii* |
| pHBA10 | *Pseudoalteromonas piscicida* |
| pHBA11 | *Pseudoalteromonas haloplanktis* |
| pHBA12 | *Cronobacter sakazakii* |
| pHBA13 | *Citrobacter youngae* |
| pHBA14 | *Citrobacter koseri* |
| pHBA15 | *Enterobacter aerogenes* |
| pHBA16 | *Enterobacter cloacae* |
| pHBA17 | *Pseudomonas putida* |
| pHBA18 | *Morganella morganii* |
| pHBA19 | *Azotobacter vinelandii* |
| pHBA20 | *Shewanella putrefaciens* |
| pHBA21 | *Cupriavidus taiwanensis* |

(4) Construction of Transgenic Strains for 4-Hydroxy Benzoate Producing Gene (Chorismate-Pyruvate Lyase Gene)

Using the above-described plasmids pHBA1 to pHBA21, transformation of *Corynebacterium glutamicum* R was performed by electroporation (Agric. Biol. Chem., Vol. 54, 443-447 (1990) and Res. Microbiol., Vol. 144, 182-135 (1993)), and each of the transgenic strains was applied to A agar medium containing 50 µg/mL of kanamycin.

A growing strain on the culture medium was subjected to liquid culture in the usual manner. Plasmid DNA was extracted from the culture and cut using the restriction enzyme to confirm the inserted plasmid. As a result, introduction of the above-constructed plasmids pHBA1 to pHBA21 was confirmed.

The obtained strains were named *Corynebacterium glutamicum* HBA-1 to HBA-21. The outline of gene recombination in the above-obtained strains is shown in Table 2.

*Corynebacterium glutamicum* HBA-2 was deposited in Incorporated Administrative Agency National Institute of Technology and Evaluation, KITE Patent Microorganisms Depositary (2-5-8 Kazusakamatari, Kisarazu-shi, Chiba 292-0818 Japan) (deposited domestically on Mar. 27, 2014 and internationally under the Budapest Treaty on Feb. 23, 2015, Accession Number: NITE BP-01838). This strain is available to the public under the conditions specified in 37 CFR1.808.

TABLE 2

4-Hydroxy benzoate-producing gene transgenic strains

| Strain | Plasmid | Origin of 4-hydroxy benzoate producing gene |
| --- | --- | --- |
| HBA1 | pHBA1 | *Pantoea ananatis* |
| HBA2 | pHBA2 | *Providencia rustigianii* |
| HBA3 | pHBA3 | *Providencia stuartii* |
| HBA4 | pHBA4 | *Providencia sneebia* |
| HBA5 | pHBA5 | *Providencia rettgeri* |
| HBA6 | pHBA6 | *Providencia alcalifaciens* |
| HBA7 | pHBA7 | *Providencia burhodogranariea* |
| HBA8 | pHBA8 | *Escherichia coli* |
| HBA9 | pHBA9 | *Escherichia fergusonii* |
| HBA10 | pHBA10 | *Pseudoalteromonas piscicida* |
| HBA11 | pHBA11 | *Pseudoalteromonas haloplanktis* |
| HBA12 | pHBA12 | *Cronobacter sakazakii* |
| HBA13 | pHBA13 | *Citrobacter youngae* |
| HBA14 | pHBA14 | *Citrobacter koseri* |
| HBA15 | pHBA15 | *Enterobacter aerogenes* |
| HBA16 | pHBA16 | *Enterobacter cloacae* |
| HBA17 | pHBA17 | *Pseudomonas putida* |
| HBA18 | pHBA18 | *Morganella morganii* |
| HBA19 | pHBA19 | *Azotobacter vinelandii* |
| HBA20 | pHBA20 | *Shewanella putrefaciens* |
| HBA21 | pHBA21 | *Cupriavidus taiwanensis* |

Example 2

Comparison of Chorismate-Pyruvate Lyase Activity Among *Corynebacterium Glutamicum* 4-Hydroxy Benzoate-Producing Gene Transgenic Strains Each of the *Corynebacterium glutamicum*/4-HBA-producing gene transgenic strains prepared in Example 1 (see Table 1) was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+ 0.042% (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin and was left stand in the dark at 33° C. for 15 hours.

An inoculation loop of each of the *Corynebacterium glutamicum*/4-HBA-producing gene transgenic strains grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+ 0.042% (w/v) $MnSO_4 \cdot 2H_2O$, 1 mL of 0.02% (w/v) biotin solution, 2 mL of 0.01% (w/v) thiamin solution, 2 g of yeast, extract, 1 g of vitamin assay casamino acid, and 40 g of glucose were suspended in 1 L of distilled water) containing 50 μg/mL of kanamycin and was aerobically cultured with shaking at 33° C. for 15 hours.

Each kind of the bacterial cells cultured and proliferated as above was collected by centrifugation (8,000 rpm, 4° C., 10 minutes). After disrupting the bacterial cells by sonication, centrifugation (15,000 rpm, 4° C., 20 minutes) was performed. Using the supernatant of the cell lysate as a crude enzyme liquid, chorismate-pyruvate lyase activity was determined by the following method. The crude enzyme liquid, 50 mM Tris-HCl (pH 7.5), 0.5 mM of chorismate Ba salt, 0.2 mM of NADH, 0.2 M of NaCl and 5 units of lactate dehydrogenase were mixed, the reaction was allowed to proceed at 33° C., and the decrease in absorbance of NADH at 340 nm was monitored to analyze the initial rate of the reaction. From the initial rate of the reaction and the protein concentration, the specific activity was calculated (the amount of the enzyme that produces 1 μmol of 4-HBA per minute was defined as 1 unit). (After the reaction mixture was filtered, the resulting 4-HBA was subjected to HPLC for direct detection of the peak of 4-HBA (Cosmosil C18 ARII made by Nacalai Tesque, mobile phase: 20% methanol and 0.07% perchloric acid) to separately confirm that the two assay methods were similar in quantitative performance.)

As the results in Table 3 show, in each of the strains HBA1 to HBA 21, the aimed chorismate-pyruvate lyase activity was detected. In particular, regarding the ubiC genes of *Pantoea ananatis* and *Cronobacter sakazakii*, markedly higher activity was shown.

Also, regarding other 4-hydroxy benzoate-producing genes of *Providencia rustigianii*, *Providencia stuartii*, *Providencia sneebia*, *Providencia rettgeri*, *Providencia alcalifaciens*, *Providencia burhodogranariea*, *Escherichia coli*, *Escherichia fergusonii*, *Pseudoalteromonas piscicida*, *Pseudoalteromonas haloplanktis*, *Cronobacter sakazakii*, *Citrobacter youngae*, *Citrobacter koseri*, *Enterobacter aerogenes*, *Enterobacter cloacae*, *Pseudomonas putida*, *Morganella morganii*, *Azotobacter vinelandii*, *Shewanella putrefaciens*, and *Cupriavidus taiwanensis*, chorismate-pyruvate lyase activity was detected. Using *Corynebacterium glutamicum* wild strain (having an empty vector only), a similar experiment was conducted. In this case, 4-HBA production was not observed.

TABLE 3

Comparison of chorismate-pyruvate lyase activity

| Strain | Host strain | Origin of 4-hydroxy benzoate producing gene | Enzymatic activity (mU · $mg^{-1}$) |
|---|---|---|---|
| HBA1 | *Corynebacterium glutamicum* R | *Pantoea ananatis* | 339 |
| HBA2 | | *Providencia rustigianii* | 145 |
| HBA3 | | *Providencia stuartii* | 83 |
| HBA4 | | *Providencia sneebia* | 103 |
| HBA5 | | *Providencia rettgeri* | 47 |
| HBA6 | | *Providencia alcalifaciens* | 20 |
| HBA7 | | *Providencia burhodogranariea* | 13 |
| HBA8 | | *Escherichia coli* | 118 |
| HBA9 | | *Escherichia fergusonii* | 29 |
| HBA10 | | *Pseudoalteromonas piscicida* | 192 |
| HBA11 | | *Pseudoalteromonas haloplanktis* | 100 |
| HBA12 | | *Cronobacter sakazakii* | 372 |
| HBA13 | | *Citrobacter youngae* | 123 |
| HBA14 | | *Citrobacter koseri* | 67 |
| HBA15 | | *Enterobacter aerogenes* | 118 |
| HBA16 | | *Enterobacter cloacae* | 113 |
| HBA17 | | *Pseudomonas putida* | 75 |
| HBA18 | | *Morganella morganii* | 71 |
| HBA19 | | *Azotobacter vinelandii* | 60 |
| HBA20 | | *Shewanella putrefaciens* | 37 |
| HBA21 | | *Cupriavidus taiwanensis* | 8 |

Example 3

Comparison of Product Inhibition on Chorismate-Pyruvate Lyase Activity Among *Corynebacterium Glutamicum* 4-HBA-Producing Gene Transgenic Strains (Comparison Based on $IC_{50}$)

Using the supernatants of the cell lysates of the strains of HBA-1 to HBA-21 prepared in Example 2, inhibition by the product, 4-HBA, was examined.

As a result, chorismate-pyruvate lyase of, in particular, the genus *Providencia*, i.e., *Providencia rustigianii*, *Providencia stuartii*, *Providencia sneebia*, *Providencia rettgeri*, *Providencia alcalifaciens*, and *Providencia burhodogranariea* were less inhibited by 4-HBA as compared to chorismate-pyruvate lyase of different genera (Table 4).

TABLE 4

Comparison of product inhibition on chorismate-pyruvate lyase activity among *Corynebacterium glutamicum* 4-HBA-producing gene transgenic strains (comparison based on $IC_{50}$)

| Strain | Host strain | Origin of 4-hydroxy benzoate producing gene | $IC_{50}$ (μM) |
|---|---|---|---|
| HBA1 | *Corynebacterium glutamicum* R | *Pantoea ananatis* | 69 |
| HBA2 | | *Providencia rustigianii* | 364 |
| HBA3 | | *Providencia stuartii* | 368 |
| HBA4 | | *Providencia sneebia* | 338 |
| HBA5 | | *Providencia rettgeri* | 394 |
| HBA6 | | *Providencia alcalifaciens* | 301 |
| HBA7 | | *Providencia burhodogranariea* | 401 |
| HBA8 | | *Escherichia coli* | 67 |
| HBA9 | | *Escherichia fergusonii* | 79 |
| HBA10 | | *Pseudoalteromonas piscicida* | 73 |
| HBA11 | | *Pseudoalteromonas haloplanktis* | 78 |
| HBA12 | | *Cronobacter sakazakii* | 76 |
| HBA13 | | *Citrobacter youngae* | 67 |
| HBA14 | | *Citrobacter koseri* | 83 |
| HBA15 | | *Enterobacter aerogenes* | 73 |

TABLE 4-continued

Comparison of product inhibition on chorismate-pyruvate lyase activity among *Corynebacterium glutamicum* 4-HBA-producing gene transgenic strains (comparison based on IC$_{50}$)

| Strain | Host strain | Origin of 4-hydroxy benzoate producing gene | IC$_{50}$ (μM) |
|---|---|---|---|
| HBA16 | | *Enterobacter cloacae* | 105 |
| HBA17 | | *Pseudomonas putida* | 68 |
| HBA18 | | *Morganella morganii* | 61 |
| HBA19 | | *Azotobacter vinelandii* | 69 |
| HBA20 | | *Shewanella putrefaciens* | 130 |
| HBA21 | | *Cupriavidus taiwanensis* | 149 |

TABLE 5

Experiment of 4-HBA production from glucose using *Corynebacterium glutamicum* 4-HBA-producing gene transgenic strains

| Strain | Host strain | Origin of 4-hydroxy benzoate producing gene | Concentration of produced 4-hydroxy benzoate (mM) (After 24 hours) |
|---|---|---|---|
| HBA1 | *Corynebacterium glutamicum* R | *Pantoea ananatis* | 0.70 |
| HBA2 | | *Providencia rustigianii* | 1.90 |
| HBA3 | | *Providencia stuartii* | 1.15 |
| HBA8 | | *Escherichia coli* | 0.67 |
| HBA12 | | *Cronobacter sakazakii* | 1.48 |

Example 4

Experiment of 4-HBA Production from Glucose Using *Corynebacterium Glutamicum* 4-HBA-Producing Gene Transgenic Strains Each of the *Corynebacterium glutamicum*/4-HBA-producing gene transgenic strains prepared in Example 1 (see Table 1) was applied to A agar medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+ 0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin and was left stand in the dark at 33° C. for 15 hours.

An inoculation loop of each of the *Corynebacterium glutamicum*/4-HBA-producing gene transgenic strains grown on a plate as above was inoculated into a test tube containing 10 mL of A liquid medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+ 0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) containing 50 μg/mL of kanamycin and also 2% of calcium carbonate and was aerobically cultured with shaking at 33° C. for 24 hours.

The culture obtained after the growth under the above-described conditions was centrifuged (15,000 rpm at 4° C. for 10 minutes), and the obtained supernatant was used for quantitative determination of 4-HBA by HPLC.

As the results in Table 5 show, *Corynebacterium glutamicum* HBA-1, HBA-2, HBA-3, HBA-8, and HBA-12 produced the aimed 4-HBA. Among them, the strains having a 4-HBA-producing gene of *Providencia rustigianii*, *Providencia stuartii*, or *Cronobacter sakazakii* had a higher, i.e., more preferable 4-HBA-producing ability than the strains having a 4-HBA-producing gene of *E. coli* or *Pantoea ananatis*. The strain that showed the highest 4-HBA-producing ability was the one having a 4-HBA-producing gene of *Providencia rustigianii*. Using *Corynebacterium glutamicum* wild strain (as a control having an empty vector only), a similar experiment was conducted. In this case, 4-HBA production was not observed.

Example 5

Test for Suitability as a Host for 4-HBA Production (Influence of 4-HBA on Aerobic Growth)

A growth inhibition test in aerobic culture was performed to examine the influence of 4-HBA on *Corynebacterium glutamicum*, *Escherichia coli*, *Pseudomonas putida*, and *Rhodobacter sphaeroides*. *Pseudomonas putida* S12, which was used for the test, is reported to be a solvent-resistant strain to produce 4-HBA via tyrosine.

*Corynebacterium glutamicum* was applied to A agar medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) and was left stand in the dark at 33° C. for 15 hours.

An inoculation loop of *Corynebacterium glutamicum* R strain grown on a plate as above was inoculated into a test tube containing 10 mL of A liquid medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+ 0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) and was aerobically cultured with shaking at 33° C. for 15 hours.

The *Corynebacterium glutamicum* R strain grown in the above conditions was inoculated into 10 mL of A liquid medium in such a way that the initial bacterial cell concentration would be OD$_{610}$=0.05, 4-HBA was added at the same time in such a way that the final concentration would be 0, 100, 200, 250, or 300 mM, and aerobic culture was performed with shaking at 33° C. The growth of the bacterial cells was determined by absorbance measurement at OD$_{610}$.

*Escherichia coli* JM109 was applied to LB agar medium (1% polypeptone, 0.5% yeast extract, 0.5% NaCl and 1.5% agar) and was left stand in the dark at 37° C. for 15 hours.

An inoculation loop of the *Escherichia coli* JM109 grown on a plate as above was applied to LB liquid medium (1% polypeptone, 0.5% yeast extract, and 0.5% NaCl), and aerobic culture was performed with shaking at 37° C. for 13 hours.

The *Escherichia coli* JM109 grown in the above conditions was inoculated into 100 mL of LB liquid medium in such a way that the initial bacterial cell concentration would be OD=0.05, 4-HBA was added at the same time in such a way that the final concentration would be 0, 100, or 200 mM, and aerobic culture was performed with shaking at 37° C.

The growth of the bacterial cells was determined by absorbance measurement at $OD_{610}$.

Pseudomonas putida S12 was applied to LB agar medium (1% polypeptone, 0.5% yeast extract, 0.5% NaCl and 1.5% agar) and was left stand in the dark at 30° C. for 15 hours.

An inoculation loop of the Pseudomonas putida S12 grown on a plate as above was applied to LB liquid medium (1% polypeptone, 0.5% yeast extract, and 0.5% NaCl), and aerobic culture was performed with shaking at 30° C. for 13 hours.

The Pseudomonas putida S12 grown in the above conditions was inoculated into 100 mL of LB liquid medium in such a way that the initial bacterial cell concentration would be $OD_{610}$=0.05, 4-HBA was added at the same time in such a way that the final concentration would be 0, 100, 200, or 300 mM, and aerobic culture was performed with shaking at 30° C. The growth of the bacterial cells was determined by absorbance measurement at $OD_{610}$.

Rhodobacter sphaeroides was applied to LB agar medium (1% polypeptone, 0.5% yeast extract, 0.5% NaCl and 1.5% agar) and was left stand in the dark at 30° C. for 20 hours.

An inoculation loop of the Rhodobacter sphaeroides grown on a plate as above was applied to LB liquid medium (1% polypeptone, 0.5% yeast extract, and 0.5% NaCl), and aerobic culture was performed with shaking at 30° C. for 13 hours.

The Rhodobacter sphaeroides grown in the above conditions was inoculated into 100 mL of LB liquid medium in such a way that the initial bacterial cell concentration would be OD=0.1, 4-HBA was added at the same time in such a way that the final concentration would be 0, 100, or 200 mM, and aerobic culture was performed with shaking at 30° C. The growth of the bacterial cells was determined by absorbance measurement at $OD_{610}$.

FIG. 1 shows analysis results of the influence of 4-HBA addition on aerobic growth.

The growth of Escherichia coli was significantly affected by 100 mM 4-HBA and completely inhibited by 200 mM 4-HBA.

The growth of Pseudomonas putida S12 (reported as a solvent-resistant strain) was completely inhibited by 200 mM 4-HBA.

The growth of Rhodobacter sphaeroides was completely inhibited by 100 mM 4-HBA.

In contrast, Corynebacterium glutamicum was able to grow even in the presence of 200 mM 4-HBA, which completely inhibited the growth of Escherichia coli, Pseudomonas putida S12, and Rhodobacter sphaeroides. Further, Corynebacterium glutamicum was able to grow even in the presence of 250 mM 4-HBA, and grew in 28 hours after the start of the culture to the same extent as in the presence of 200 mM 4-HBA (about 65% of the $OD_{610}$ of wild strain) although the data are not shown here.

Thus, it was shown that Corynebacterium glutamicum has a higher resistance to 4-HBA as compared with Escherichia coli, Pseudomonas putida S12, and Rhodobacter sphaeroides, and is highly suitable as a host in 4-HBA production.

INDUSTRIAL APPLICABILITY

According to the process of the present invention, using microorganisms, 4-HBA can be produced from glucose or the like with a practical efficiency.

The invention claimed is:

1. A transformant capable of producing 4-hydroxybenzoic acid or a salt thereof, the transformant being constructed by introducing a gene which encodes an enzyme having chorismate-pyruvate lyase activity into a coryneform bacterium as a host,
wherein the gene which encodes an enzyme having chorismate-pyruvate lyase activity is the DNA of the following (a) or (b);
(a) a DNA consisting of the sequence of SEQ ID NO:2,
(b) a DNA which hybridizes to a DNA consisting of a complementary sequence of the DNA of (a) under stringent conditions or which consists of a sequence having 90% or more of homology with the sequence of (a), and which encodes a polypeptide having chorismate-pyruvate lyase activity.

2. The transformant of claim 1, wherein the transformant is *Corynebacterium glutamicum* HBA-2 (Accession Number: NITE BP-01838).

3. A process for producing 4-hydroxybenzoic acid or a salt thereof, which comprises a step of culturing the transformant of claim 1 in a reaction mixture containing at least one starting compound selected from the group consisting of a sugar, a compound from which the transformant is capable of producing chorismic acid by metabolism, and chorismic acid or a salt thereof, and a step of recovering 4-hydroxybenzoic acid or a salt thereof from the reaction mixture.

4. The process of claim 3, wherein the transformant is cultured under aerobic conditions where the transformant does not grow.

* * * * *

SEQUENCE LISTING

```
<160> NUMBER OF SEQ ID NOS: 63

<210> SEQ ID NO 1
<211> LENGTH: 513
<212> TYPE: DNA
<213> ORGANISM: Pantoea ananatis

<400> SEQUENCE: 1
atgacgcaag acccgctccg ttcgttacgt tcacttaact ggctggcgct ggacgatgcc      60
gcattgacgc aaccgcttcg tgactggcta atggaagagg attccatgac gcgacgcttt     120
gaacagcatt gccagaaggt cagggtggaa cctgtacgtg aggactttat ctccgccgat     180
gaactcggcg atgaaggggc attactccct gccgatcagc gtttctggct gcgagaagtc     240
attctctacg gggatgagga accttggctg gcagggcgca cgctggtgcc agaaagtacc     300
ctcaacggcc cggaagcgat gttacagcaa ctcggtacgc gcccgctggg gcgttatctg     360
ttctcgtcat caacgctgac ccgcgatttc attgagcctg gccgcgttga tgcgctctgg     420
ggacgccgct cgcgcctgcg actgtcaggg aaaccgctgc tgttaacgga actgttttta     480
ccggcttcgc cgctctatcg tgatcaaggt taa                                  513

<210> SEQ ID NO 2
<211> LENGTH: 519
<212> TYPE: DNA
<213> ORGANISM: Providencia rustigianii

<400> SEQUENCE: 2
atgcatgaaa caatttttac ccatcatccc attgattggc taaacgagga tgatgagtca     60
```

```
gttcctaaca gtgtactaga ttggctgcaa gagcgtggtt caatgactaa acggttcgag    120
cagcattgcc aaaaagtcac ggtaattccc tatttagagc gctatatcac tccagagatg    180
ctgagcgctg atgaagccga gcgtttaccc gaaagtcaac gttactggtt gcgagaagtc    240
attatgtatg gggataatat tccgtggttg ataggcagaa cattgatccc tgaagagacc    300
ctcaccaacg atgataaaaa gctggtggac attggtcgtg tgccattagg gcgttacctt    360
tttagtcatg atagtcttac ccgagattat attgatattg caccagtgc ggatcgttgg    420 gtgcgacgtt ctctgctgag attatctcaa aagcccttat tattaactga aatattttta    480
cctgaatcac ctgcatatag ataactatct aacataatc                          519
```

<210> SEQ ID NO 3
<211> LENGTH: 537
<212> TYPE: DNA
<213> ORGANISM: Providencia stuartii

<400> SEQUENCE: 3

```
atggatgaaa cgcttttat ctctcacccg ataacatggc tatcagaaga tgatgacctt     60
gttcctgaaa atgttttaga ttggctacat gaactagggt cgatgacaaa acgcttagag    120
cagcattgcc aacgtgtcac ggttgttcct tatacgcaac gttatgtgac tcaagaggca    180
ttgagcgaag aagaagcggc gtgtttacct gtcagtgaat attattggtt acgtgaagtc    240
attatgtatg gtgataatat tccatggtta cttggacgac gttaattcc acaggagaca    300 ttgactggtg aagaccggaa acttattgat atcggtgctg taccgttagg gcgttatctc    360
tttagccatg ataatctttc ccgtgattat attcatatag ggcagcaaaa tttgcgatgg    420
atccgccgct ctctattaag attatctgaa aaacctttat tattaaccga actgttttta    480
cctgaatcac ctgcatataa aagataaaaa ataaaaggag cacaacaaat ggaggga      537
```

<210> SEQ ID NO 4
<211> LENGTH: 539
<212> TYPE: DNA
<213> ORGANISM: Providencia sneebia

<400> SEQUENCE: 4

```
atggatgata cgcttttac ctctcacccg ataacatggt tatcagagac tgataatgtt     60
attcctgaaa atatgttaag ttggttacaa gaactcgggt caatgacaaa gcgcttagaa    120
caatattgcc agtctttgac tgtcacccct tatgtgcaaa aatatgtttc cagaaacatg    180
ctgagtgatg atgaagctca atgtttacct gaaagctcaa gttattggct aagagaagtg    240
attatctatg gggataatat cccttggttg ctagggcgaa cgctaattcc gcaagaaaca    300
ttgagtggcg atgaccaaag aattgtcgat attggtacgc tgccttagg ccgttatcta    360 tttagtcatg ataatctgac tcgtgattat attcatattg gcaacagga gcagcgatgg    420 ctgcgtcgtt cgcgattaag gctatcgaat aatccttat tattaactga attgttttta    480
cctgaatcac ctgcatataa aagataaaaa ataaaaggag catgacaagt gaagggaag    539
```

<210> SEQ ID NO 5
<211> LENGTH: 504
<212> TYPE: DNA
<213> ORGANISM: Providencia rettgeri

<400> SEQUENCE: 5

```
atggatgaaa cgcttttac ttctcagccg attcactggc tggcggagaa cgataaaata     60
gtgcctgcca atgtattaga ttggctatta gagctcggct ccatgacaaa acgtttgag    120
```

```
cagcatagcc agcaagttac cgtgatacct tatttagagc gctatataac acaagataag    180
ctgagtgcag atgaaatgct gtctttacct gaaagccaac gttattgggt cagagaagtt    240
gtcatgtatg gagatggtat cccttggtta ctgggccgaa cgataatccc tgaagaaaca    300
ctgactgatg atgaccagca actggtagat attgggagaa tgccgttagg gcgttattta    360
tttagccgtg acagcttaac tcgagattat attcatattg gttcttgcgc aaaccgttgg    420
gtacgttgtt ctcggttaag attatcggat aaacccttac tattaacaga aatatttta    480 cctgaatcac ctgcatatcg ttaa                                           504

<210> SEQ ID NO 6
<211> LENGTH: 505
<212> TYPE: DNA
<213> ORGANISM: Providencia alcalifaciens

<400> SEQUENCE: 6
atgcatgaaa cgatttttac ctctcatcct ataagttggt tcgtagaagg cgaagagagt     60
gttcctgaaa atgtattagg ttggttgcaa gagcaaaggt cgatgaccaa acggtttgag    120
cagcattgtc agaaagtgac ggtgatacct tatttagaac gctatatctc actggatatg    180
ctcaccaccg acgaacaaaa atgcttacca attagtgagc gttattggct acgggaagtg    240
attatgtatg gggataatat cccttggttg attggcagaa cgctgatccc agaagagacg    300
ctcaccgata atgacaaaaa attagtcgag cttgggcgag tcccattagg gcgctatctc    360
tttagtcatg aacacctaac ccgagattat attgaaatgg caccagtgc tgaccgctgg    420 gttcgccgtt ccttacttag actgtcccaa aaaccattat tattaaccga aatatttta    480 cctgaatcac ctgcatatag ataac                                          505

<210> SEQ ID NO 7
<211> LENGTH: 542
<212> TYPE: DNA
<213> ORGANISM: Providencia burhodogranariea

<400> SEQUENCE: 7
atggatgaaa cgcttttac ctctcacccg ataacgtggc taccagaggc cgatgacctt      60
gttcctgata atattttaga ctggttgcat gagcttgggt caatgacaaa acgtttagag    120
cagcactgcc agtgtgttac cgttatccct tgtgcgcagc gatatgtgac taaagaagct    180
ctcagtgatg atgaaactca atgtttaccg gtgagtgagt actattggtt acgggaggtt    240
attatgtatg gtgataatat tccctggtta ctcggccgaa cactaattcc gcaagaaaca    300
ttgaccggtg aagaccaaaa gctcattgat attggtgctg taccattagg gcgttatcta    360
tttagtcatg ataatcttac ccgggattat attcatatag ggcagcaaaa ttctcgatgg    420
ctccgtcgct ctcgattaag gttatcaaac aaaccgttat tattaactga attattta     480 cctgaatcac ctgcttataa aagataaaaa gtaaaggag cacgacaagt ggagggaagt    540
at                                                                   542

<210> SEQ ID NO 8
<211> LENGTH: 498
<212> TYPE: DNA
<213> ORGANISM: Escherichia coli

<400> SEQUENCE: 8
atgtcacacc ccgcgttaac gcaactgcgt gcgctgcgct attgtaaaga gatccctgcc     60
```

```
ctggatccgc aactgctcga ctggctgttg ctggaggatt ccatgacaaa acgttttgaa      120
cagcagggaa aaacggtaag cgtgacgatg atccgcgaag gtttgtcga gcagaatgaa      180 atccccgaag aactgccgct gctgccgaaa gagtctcgtt actggttacg tgaaattttg      240
ttatgtgccg atggtgaacc gtggcttgcc ggtcgtaccg tcgttcctgt gtcaacgtta      300
agcgggccgg agctggcgtt acaaaaattg gtaaaacgc cgttaggacg ctatctgttc       360
acatcatcga cattaacccg ggactttatt gagataggcc gtgatgccgg gctgtggggg      420
cgacgttccc gcctgcgatt aagcggtaaa ccgctgttgc taacagaact gttttaccg       480 gcgtcaccgt tgtactaa                                                    498
```

<210> SEQ ID NO 9
<211> LENGTH: 663
<212> TYPE: DNA
<213> ORGANISM: Escherichia fergusonii

<400> SEQUENCE: 9

```
atgctgattt tgcaacaact ggtgcgtctt ctggcgcacc ttttttatc atttttgcg        60 attgttgcgt ttttgttgcg caatagatca cttaattttg tttccttctc ccgtaatctc     120
ttttctgcga tacaatgcct tcacgttata gaacggagag ttcgcatgtc acatcccgcg     180
ttaacgcaac tgcgtgcgct cgctattttt gctgagattc cggcgcttga tcccgcacaa     240
ctcgactggt tattactgga agattccatg accaaacgtt ttgagcagca gggaaaaaag     300
gtgagcgtga cagtaatccg cgaaggcttt gtcgggcaac aagatgttgc cctggagtta     360
tcgcagttgc cgcaagagcc tcgctactgg ctgcgggaaa ttttactttg cgcagatggt     420
gaaccctggc ttgcggggcg cactgtggtg ccagaatcaa cgttatctgg ccctgaactg     480
gcattacaaa aactgggtaa gacccgttg gggcgctacc tgtttacatc atcaacgttg      540
agccgtgatt ttattgagat tggtcgtgat gcagagctat gggggcggcg ttcacgtctg     600
cggttaagcg gtaagcccct gatgcttact gaactgtttt tgcctgcatc accgttgtac     660
taa                                                                    663
```

<210> SEQ ID NO 10
<211> LENGTH: 554
<212> TYPE: DNA
<213> ORGANISM: Pseudoalteromonas piscicida

<400> SEQUENCE: 10

```
atgcctttgc aattaccctt agagctccct tggctgaaga acacacagtt ggtggatgtt      60
gagccagcac tttctcctta tttactagag gctcaatctc taaccgcaaa attgaaagaa     120
acttgtgaaa ggttttctgt gactgtgctt gctaatgagt tcaggagcgc tcctgaagcg     180
ttacgtacgg atctttctga acaggtttgg tgccgagaag taacgttaaa ttgtaacggt      240
aaagcagctg tatttggaca agttggctc aatgaggacg catgtactgt cggaatggat     300
gcaattggtg agacaccttt gggtgagtta ctgtttactg attcaaattg gcagcgcgga     360
acccttgagt tcttcgtttt atctactgcc gactatccgg cgctgattga acttattgca     420
cccacaactg gcgtcgcccc agagcgttta tttgctagaa gaagctggtt taaaaacggc     480
aaagcaaaga ttttagtttg tgaagtcttt atatcggaaa gctttatga ttgaccacca      540 gaaatggcag gctt                                                       554
```

<210> SEQ ID NO 11
<211> LENGTH: 546

```
<212> TYPE: DNA
<213> ORGANISM: Pseudoalteromonas haloplanktis

<400> SEQUENCE: 11
atgattactt tccctgtttc attatctgct gattggcaga gtaccgctca agtaactggc      60
ttatctaacg ctgagaaaga gtggttattt gaaccgcatt ctttaacggc taaattaaaa     120
agtcagtctc agcgttttgc tgtaaaagtg ttgagtgagc aaaaagtaga cctttcgcaa     180
tcacagcaaa cgctattaag tgagcaggta agtacagtac ttaaccgtga agtgttactg     240
ttgtgtgatg aacaaccgat tgtttatgct caaagttggt tgccagtaac aagcaataat     300
acaaacaatc agctgcacaa tatgggagaa cgcccgttag gtgatgttat ctttcaagat     360
cctgcgttaa ggcgcactga tattgaaatt gctcgctttg atgataatca cccattgcaa     420
tcactggtga gcgaacttaa tttaccgaat cgctctttac tgggcagacg cagcgtattt     480
tctttacata actacaaatt tttagtttgt gaagtttttt taccaggagc gtatttgtac     540
tcatga                                                                546

<210> SEQ ID NO 12
<211> LENGTH: 534
<212> TYPE: DNA
<213> ORGANISM: Cronobacter sakazakii

<400> SEQUENCE: 12
atgtcccatc ccgcgctgag acaactgcgc gcgttgtcct ttttgacga tatcagcacg       60
cttgatagtt cgctgctcga ctggctgatg ctggaagatt ccatgacccg ccgtttcgaa     120
ggcttttgcg agcgcgtgac ggtcgacatg ctgtttgagg gctttgtcgg ccccgaggcg     180
ctggaggaag agggcgagtt tttgcctgat gagccgcgct actggctgcg cgaaatcctg     240
ctgtgcggcg acggcgtgcc gtggctggtt gggcgcacgc tggtgccgga gtctacactt     300
tgtgggccgg agctggcgtt gcagcagctc ggtaccacgc cgctgggccg ttatctgttt     360
acctcatcca ccctcacgcg tgattttatc cagccgggcc gcagcgacga actctgggga     420
cgccgctctc tgctgaggct ttccggcaaa ccgctgctgc tgactgaact gtttttacct     480
gcatcaccct gtacggagag ggaaaaataa tggagtggag cctgacgcag aata           534

<210> SEQ ID NO 13
<211> LENGTH: 498
<212> TYPE: DNA
<213> ORGANISM: Citrobacter youngae

<400> SEQUENCE: 13
atgccacacc ctgcgttaac gcaactgcgt gcgctgcgtt attttgatga gatcccggcg      60
ctggaccccg cagctgctcga ctggttgtta ctggaagatt cgatgaccaa cgttttgag    120
cagcagggaa acaagtcac cgttacgttg attcgcgaag cgttcgttgg caaaatgag     180
gtggctgaag aactgatgct gctgcctaaa gaatcccgct actggttacg cgaaatcctg     240
ttatgcgcgg atggtgagcc ctggcttgcc gggcgtaccg tggtgcctga tcaaccctg     300
tgcggccctg aactggcctt acaaaatctg gggaaaaccc cgctcggacg ctacctgttt     360
acgtcatcga cattgacccg agattttatt gagattggcc gcgatgcagc gctgggggg    420
cgacgttccc gcctgcggct gagcggtaag ccattgatgc ttaccgagct ttttctacct     480
gcatcgccgt tgtactga                                                   498

<210> SEQ ID NO 14
```

<211> LENGTH: 498
<212> TYPE: DNA
<213> ORGANISM: Citrobacter koseri

<400> SEQUENCE: 14

```
atgtcacacc ctgcgttaac gcaactgcgt gcgctgcgct attttaaaga gattcctgcg     60
ctggattccc ggttgctcga ctggttactt ctggaagatt ccatgaccaa acgttttgag    120
caagaaggga aacgggtaag cgtgacattg cttcgggaag cgtttgttgg tccacatgaa    180
gtggctgaag aggtggcgct gctaccggtc gaatcccgct actggttacg tgaaattttg    240
ttatgtgcag acggcgaacc ctggcttgcc gggcgtaccg tcgtgcctga atcaacgttg    300
tgcggccctg agctggcctt acaaaatctg gaaaaacgc cgttagggcg ctacctgttt    360
acatcatcaa cgttgacccg agattttatt gagattggtc gtgatgccgc actgtggggg    420
cgtcgttccc gcctgcgtct gagcggtaag ccgctgatgc ttaccgagct gttttttgccc    480
gcatcaccgt tgtattaa                                                   498
```

<210> SEQ ID NO 15
<211> LENGTH: 498
<212> TYPE: DNA
<213> ORGANISM: Enterobacter aerogenes

<400> SEQUENCE: 15

```
atgccacatc ctgcgcttac gcaactgcgt gcgctgcgct attttgccgc catacccgag     60
ctggacgcgc gctgcgcga ctggctgttg ctggaagact caatgaccaa acgctttgag    120
caacaaggga aaaggtcac cgtgaccatg attaacgaag gtttcgtcgg gcgcgacgcg    180
ctggcgggcg aagaagccct gctgccggaa gaggcgcggt attggctgcg ggagatcatt    240
cttttgcgcc atggcgaacc ctggcttgcc ggtcgtactc tcgtgccgga atcgacgcta    300
tgcggcccgg aattagccct gcagcagttg gggcagacgc cgctgggccg gtatctgttt    360
acgtcgtcga cgttaacccg tgattttatt gagattggcc gtagtgcaca gctgtggggg    420
cgacgttccc gtctccggct gagcggcaaa ccgctgctgc tgacagagct ttttctgcct    480
gcatcgccat tgtattaa                                                   498
```

<210> SEQ ID NO 16
<211> LENGTH: 498
<212> TYPE: DNA
<213> ORGANISM: Enterobacter cloacae

<400> SEQUENCE: 16

```
atgtcacacc ctgcgctaac gcaactgcgt tcgctgcgct atttcgacca aatacctgcg     60
cttgacccgc agcagcttga ctggttgctg ctggaagatt ccatgactaa acgttttgag    120
caacagggca agacggttac ggtgacgatg attcaggaag ggtttgtcac ctccgctgac    180
attgccagtg agctgccgct gttaccaaaa gaagaacgct actggttgcg tgaaattctg    240
ctctgcgcgg atggtgagcc gtggctcgcc ggacgaaccg tggtgcctga atccacccctt    300
tccgggcctg agctggcact gcaacggctg ggaaacaccc cgctcgggcg gtaccttttc    360
acctcgtctg aacttacccg ggattttatt gaaattggac gcgatgccga actgtgggga    420
cgtcgttccc gtcttcgcct gagcggtaaa ccgttaatac tgacggagct ttttttaccg    480
gcatcgccgt tgtactga                                                   498
```

<210> SEQ ID NO 17
<211> LENGTH: 558

```
<212> TYPE: DNA
<213> ORGANISM: Pseudomonas putida

<400> SEQUENCE: 17
atgtcgtacg aatccccgca agcagccgct gtcgcgtggc tgccgtattc acagctggcg      60
accgacatcg accagcccac ccttgactgg ctgttcgacg agggctcgct gacccgccgc     120
ctgacccgtc tgtccattga tcacttttcc gtcaccccgt tgttcgaggg ctggcagccg     180
ctgcgcgatg acgaatgcca ggcgctgggc atcgctgccg cgccgaagg ctgggtgcgc     240 gaagtgtatc tgcgcggcca tggccaacct tgggtattcg cccgcagcgt ggccagccgc     300
agcgccctgg aacgtggtgg cctggacctg gaaaccttgg gcagccgctc gctgggcgag     360
ctgctgttct gcgaccaggc gttcatccgt catccactcg aagtgtgcac ttatccacag     420
gcctggctgc cgtccgaagc tgcacatgcg gcgctttggg gccgccgctc gcgcttcgag     480
cgcaacggcc tggacctgct ggtggcagaa gtgttcctgc cggcattgtg gcaagcggcc     540
aaggaggaaa accgctga                                                   558

<210> SEQ ID NO 18
<211> LENGTH: 529
<212> TYPE: DNA
<213> ORGANISM: Morganella morganii

<400> SEQUENCE: 18
atgacacaaa cagtgataac cccccccatc cgctggtttg ataatgcgga aatgatcccc      60
gccggggtgc tggactggtt atcagaatta gggtcaatga cgcggcgctt tgaacagcac     120
tgcaatgaag tgacggtaaa accgtattgt gaaaaatata tctcccgtga agcgctgact     180
gaagaagagc agatgcatct gcccggcagt gcacgctact ggttacggga ggtggtgtta     240
tatggtgacg gggttccctg ctgaccggc cggacagtgg taccggagga gacgctgaca     300
ggggaagagc agcagttact gaaaatggga aatgtgccgc tcgggcgcta tctctttacc     360
agcggttgtc tgacgcggga ttatatccgc ttcgggctgt cagaaacgca ctgggcgcgc     420
tgttcgcggc tgtgcctggc cggtaaaccg cttctgctga ctgaagtttt tctgccggcc     480
tctccggcat accccgcata agtgaatatc tcggagaaga ataacgtgg                 529

<210> SEQ ID NO 19
<211> LENGTH: 552
<212> TYPE: DNA
<213> ORGANISM: Azotobacter vinelandii

<400> SEQUENCE: 19
atgaccgctg ctcccgcttt ccaatggctc ggcgccgacc aactgcatcc cgccccccg      60 gccgtcctgg ccgactggct gttcgacagc ggctcgctga cccgccggct gaccgccctt     120
tccgccggcc gtttcgccgt gacgccgctg ccgaaggct ggcaggtgct gcgcgacgac     180
gaatgcaccg ccctcgacgt ggtgccggc agcaccggct gggtacgcga ggtctacctg     240
ctcggcgccg agcggccctg ggtgttcgcc cgcagcgtgg cggcccgcga ggctctggcg     300
ggtttctccg gcgtactcgc cgaactcggc cggcggcccc tcggcgaact gctgttcagc     360
gacccagcct cgcccgcgg cccgctgcag gccacgcact atccgccgga ctggctgccg     420
gccgggatac gctgcccgg actctgggga cggcgctccc gtttccaccg ggaaaccctg     480
agcgtgctgg tggcggaagt cttcctgccg gagctctggc gctaccaggg aatcgacccg     540 gacacccctat aa                                                        552
```

<210> SEQ ID NO 20
<211> LENGTH: 561
<212> TYPE: DNA
<213> ORGANISM: Shewanella putrefaciens

<400> SEQUENCE: 20

| | | | | | | |
|---|---|---|---|---|---|---|
| atgaatgtga | ctagcttaag | cttcccctat | ggtgaatcta | ttcaatggtt | ttgtgctgat | 60 |
| cgtaccgata | aacttccccc | gtcaccgcta | aaagagtggt | tactcgcccc | aggcagcctg | 120 |
| acaaaaaaac | tcaaaacctg | ctgcaatcag | tttgaagtca | aagtcctcgg | tgaaggccaa | 180 |
| ctcgccccct | tcaaagatga | atatcctcag | caaggctctg | tttgggttcg | tgaagtattg | 240 |
| ctatgccttg | ataatgttcc | ttgggtgttt | gccagaacct | taatcccact | ctctttgctg | 300 |
| tctgaacgag | aagcggattt | tctcggtttg | ggttctcgtc | cccttggcga | attactcttt | 360 |
| agccaagata | actttatccc | cggcagaata | gaagtcgcca | gctttgatac | aggtagtcgt | 420 |
| cttgcacact | tagctgcaag | tttagatcaa | agggttgaac | atctcctgtg | gggacgccgt | 480 |
| cgctattttc | accacggcca | ggatgagatg | atcgtcagtg | aaatattttt | acctgcggcc | 540 |
| gagcgagcaa | tttgccagtg | a | | | | 561 |

<210> SEQ ID NO 21
<211> LENGTH: 671
<212> TYPE: DNA
<213> ORGANISM: Cupriavidus taiwanensis

<400> SEQUENCE: 21

| | | | | | | |
|---|---|---|---|---|---|---|
| atgagcgcgc | agtccgtgcg | cggctgcggc | tggagcccgc | acctggcttt | cgatgcggcg | 60 |
| atcccgccca | acctgcggcg | ctgggttacc | ggcgatgacg | gctcgctgac | ggcgcggctg | 120 |
| gtggccgcct | ccgcgcgctt | tcgcgtggcg | cggctgctgc | aggcgccgca | gcgcccgttt | 180 |
| gccgacgaat | ggcaggcgct | gggccagccc | gaccgcaccc | ccgcgctgac | gcgcgaggtg | 240 |
| ctgctgatct | gcgacgacat | ccccgccgtg | ttcgcccata | ccgtggtgcg | gctgcgccat | 300 |
| gcgcgccgcg | actggccgtt | cctgcgcggg | ctgggcgaac | gcccgctggg | cgggcgcctg | 360 |
| ttcgtcgatc | cggcggtgcg | gcgcgagccg | ttccagtttg | cgcggctgct | gccgcaccat | 420 |
| ccgctgcgcc | aggccctgca | ccgcgtgctg | ccggccatgg | cggcagtgcc | gatgctgacc | 480 |
| gcgcggcgtt | cggtgttccg | gcgcggcggc | ggcgtcatgc | tcgtgacaga | agtgttcctg | 540 |
| ccagacctgc | tgtcgcggcc | atccccgggg | accgaggcgg | taccgcatcc | caaatatatg | 600 |
| cggacgacag | accgaagccc | tgtttcgaca | cacactaccg | aaaccaagaa | agagaccacg | 660 |
| agatgaaact | g | | | | | 671 |

<210> SEQ ID NO 22
<211> LENGTH: 24
<212> TYPE: DNA
<213> ORGANISM: Artificial sequence
<220> FEATURE:
<223> OTHER INFORMATION: PCR primer

<400> SEQUENCE: 22
ctctcatatg acgcaagacc cgct                                          24

<210> SEQ ID NO 23
<211> LENGTH: 33
<212> TYPE: DNA
<213> ORGANISM: Artificial sequence
<220> FEATURE:
<223> OTHER INFORMATION: PCR primer

<400> SEQUENCE: 23
ctctcatatg ttaaccttga tcacgataga gcg                33

<210> SEQ ID NO 24
<211> LENGTH: 36
<212> TYPE: DNA
<213> ORGANISM: Artificial sequece
<220> FEATURE:
<223> OTHER INFORMATION: PCR primer

<400> SEQUENCE: 24
ctctcatatg catgaaacaa ttttttaccca tcatcc            36

<210> SEQ ID NO 25
<211> LENGTH: 42
<212> TYPE: DNA
<213> ORGANISM: Artificial sequence
<220> FEATURE:
<223> OTHER INFORMATION: PCR primer

<400> SEQUENCE: 25
ctctcatatg gattatgtta gatagttatc tatatgcagg tg      42

<210> SEQ ID NO 26
<211> LENGTH: 34
<212> TYPE: DNA
<213> ORGANISM: Artificial sequence
<220> FEATURE:
<223> OTHER INFORMATION: PCR primer

<400> SEQUENCE: 26
ctctcatatg gatgaaacgc tttttatctc tcac               34

<210> SEQ ID NO 27
<211> LENGTH: 30
<212> TYPE: DNA
<213> ORGANISM: Artificial sequence
<220> FEATURE:
<223> OTHER INFORMATION: PCR primer

<400> SEQUENCE: 27
ctctcatatg tccctccatt tgttgtgctc                    30

<210> SEQ ID NO 28
<211> LENGTH: 32
<212> TYPE: DNA
<213> ORGANISM: Artificial sequence
<220> FEATURE:
<223> OTHER INFORMATION: PCR primer

<400> SEQUENCE: 28
ctctcatatg gatgatacgc tttttacctc tc                 32

<210> SEQ ID NO 29
<211> LENGTH: 30
<212> TYPE: DNA
<213> ORGANISM: Artificial sequence
<220> FEATURE:
<223> OTHER INFORMATION: PCR primer

<400> SEQUENCE: 29
ctctcatatg cttcccttca cttgtcatgc                    30

<210> SEQ ID NO 30

<211> LENGTH: 34
<212> TYPE: DNA
<213> ORGANISM: Artificial sequence
<220> FEATURE:
<223> OTHER INFORMATION: PCR primer

<400> SEQUENCE: 30
ctctcatatg gatgaaacgc tttttacttc tcag    34

<210> SEQ ID NO 31
<211> LENGTH: 34
<212> TYPE: DNA
<213> ORGANISM: Artificial sequence
<220> FEATURE:
<223> OTHER INFORMATION: PCR primer

<400> SEQUENCE: 31
ctctcatatg ttaacgatat gcaggtgatt cagg    34

<210> SEQ ID NO 32
<211> LENGTH: 35
<212> TYPE: DNA
<213> ORGANISM: Artificial sequence
<220> FEATURE:
<223> OTHER INFORMATION: PCR primer

<400> SEQUENCE: 32
ctctcatatg catgaaacga tttttacctc tcatc    35

<210> SEQ ID NO 33
<211> LENGTH: 35
<212> TYPE: DNA
<213> ORGANISM: Artificial sequence
<220> FEATURE:
<223> OTHER INFORMATION: PCR primer

<400> SEQUENCE: 33
ctctcatatg gttatctata tgcaggtgat tcagg    35

<210> SEQ ID NO 34
<211> LENGTH: 32
<212> TYPE: DNA
<213> ORGANISM: Artificial sequence
<220> FEATURE:
<223> OTHER INFORMATION: PCR primer

<400> SEQUENCE: 34
ctctcatatg gatgaaacgc tttttacctc tc    32

<210> SEQ ID NO 35
<211> LENGTH: 30
<212> TYPE: DNA
<213> ORGANISM: Artificial sequence
<220> FEATURE:
<223> OTHER INFORMATION: PCR primer

<400> SEQUENCE: 35
ctctcatatg atacttccct ccacttgtcg    30

<210> SEQ ID NO 36
<211> LENGTH: 26
<212> TYPE: DNA
<213> ORGANISM: Artificial sequence
<220> FEATURE:
<223> OTHER INFORMATION: PCR primer

<400> SEQUENCE: 36
ctctcatatg tcacaccccg cgttaa                                      26

<210> SEQ ID NO 37
<211> LENGTH: 29
<212> TYPE: DNA
<213> ORGANISM: Artificial sequence
<220> FEATURE:
<223> OTHER INFORMATION: PCR primer

<400> SEQUENCE: 37
ctctcatatg ttagtacaac ggtgacgcc                                   29

<210> SEQ ID NO 38
<211> LENGTH: 31
<212> TYPE: DNA
<213> ORGANISM: Artificial sequence
<220> FEATURE:
<223> OTHER INFORMATION: PCR primer

<400> SEQUENCE: 38
ctctcatatg ctgattttgc aacaactggt g                                31

<210> SEQ ID NO 39
<211> LENGTH: 31
<212> TYPE: DNA
<213> ORGANISM: Artificial sequence
<220> FEATURE:
<223> OTHER INFORMATION: PCR primer

<400> SEQUENCE: 39
ctctcatatg ttagtacaac ggtgatgcag g                                31

<210> SEQ ID NO 40
<211> LENGTH: 31
<212> TYPE: DNA
<213> ORGANISM: Artificial sequence
<220> FEATURE:
<223> OTHER INFORMATION: PCR primer

<400> SEQUENCE: 40
ctctcatatg cctttgcaat taccttaga g                                 31

<210> SEQ ID NO 41
<211> LENGTH: 30
<212> TYPE: DNA
<213> ORGANISM: Artificial sequence
<220> FEATURE:
<223> OTHER INFORMATION: PCR primer

<400> SEQUENCE: 41
ctctcatatg aagcctgcca tttctggtgg                                  30

<210> SEQ ID NO 42
<211> LENGTH: 36
<212> TYPE: DNA
<213> ORGANISM: Artificial sequence
<220> FEATURE:
<223> OTHER INFORMATION: PCR primer

<400> SEQUENCE: 42
ctctcatatg attactttcc ctgtttcatt atctgc                           36

<210> SEQ ID NO 43
<211> LENGTH: 33
<212> TYPE: DNA

```
<213> ORGANISM: Artificial sequence
<220> FEATURE:
<223> OTHER INFORMATION: PCR primer

<400> SEQUENCE: 43
ctctcatatg tcatgagtac aaatacgctc ctg                              33

<210> SEQ ID NO 44
<211> LENGTH: 27
<212> TYPE: DNA
<213> ORGANISM: Artificial sequence
<220> FEATURE:
<223> OTHER INFORMATION: PCR primer

<400> SEQUENCE: 44
ctctcatatg tcccatcccg cgctgag                                     27

<210> SEQ ID NO 45
<211> LENGTH: 30
<212> TYPE: DNA
<213> ORGANISM: Artificial sequence
<220> FEATURE:
<223> OTHER INFORMATION: PCR primer

<400> SEQUENCE: 45
ctctcatatg tattctgcgt caggctccac                                  30

<210> SEQ ID NO 46
<211> LENGTH: 26
<212> TYPE: DNA
<213> ORGANISM: Artificial sequence
<220> FEATURE:
<223> OTHER INFORMATION: PCR primer

<400> SEQUENCE: 46
ctctcatatg ccacccctg cgttaa                                       26

<210> SEQ ID NO 47
<211> LENGTH: 29
<212> TYPE: DNA
<213> ORGANISM: Artificial sequence
<220> FEATURE:
<223> OTHER INFORMATION: PCR primer

<400> SEQUENCE: 47
ctctcatatg tcagtacaac ggcgatgca                                   29

<210> SEQ ID NO 48
<211> LENGTH: 27
<212> TYPE: DNA
<213> ORGANISM: Artificial sequence
<220> FEATURE:
<223> OTHER INFORMATION: PCR primer

<400> SEQUENCE: 48
ctctcatatg tcacccctg cgttaac                                      27

<210> SEQ ID NO 49
<211> LENGTH: 31
<212> TYPE: DNA
<213> ORGANISM: Artificial sequence
<220> FEATURE:
<223> OTHER INFORMATION: PCR primer

<400> SEQUENCE: 49
ctctcatatg ttaatacaac ggtgatgcgg g                                31
```

<210> SEQ ID NO 50
<211> LENGTH: 27
<212> TYPE: DNA
<213> ORGANISM: Artificial sequence
<220> FEATURE:
<223> OTHER INFORMATION: PCR primer

<400> SEQUENCE: 50
ctctcatatg ccacatcctg cgcttac                                27

<210> SEQ ID NO 51
<211> LENGTH: 32
<212> TYPE: DNA
<213> ORGANISM: Artificial sequence
<220> FEATURE:
<223> OTHER INFORMATION: PCR primer

<400> SEQUENCE: 51
ctctcatatg ttaatacaat ggcgatgcag gc                          32

<210> SEQ ID NO 52
<211> LENGTH: 26
<212> TYPE: DNA
<213> ORGANISM: Artificial sequence
<220> FEATURE:
<223> OTHER INFORMATION: PCR primer

<400> SEQUENCE: 52
ctctcatatg tcacaccctg cgctaa                                 26

<210> SEQ ID NO 53
<211> LENGTH: 28
<212> TYPE: DNA
<213> ORGANISM: Artificial sequence
<220> FEATURE:
<223> OTHER INFORMATION: PCR primer

<400> SEQUENCE: 53
ctctcatatg tcagtacaac ggcgatgc                               28

<210> SEQ ID NO 54
<211> LENGTH: 25
<212> TYPE: DNA
<213> ORGANISM: Artificial sequence
<220> FEATURE:
<223> OTHER INFORMATION: PCR primer

<400> SEQUENCE: 54
ctctcatatg tcgtacgaat ccccg                                  25

<210> SEQ ID NO 55
<211> LENGTH: 29
<212> TYPE: DNA
<213> ORGANISM: Artificial sequence
<220> FEATURE:
<223> OTHER INFORMATION: PCR primer

<400> SEQUENCE: 55
ctctcatatg tcagcggttt tcctccttg                              29

<210> SEQ ID NO 56
<211> LENGTH: 31
<212> TYPE: DNA
<213> ORGANISM: Artificial sequence
<220> FEATURE:

<223> OTHER INFORMATION: PCR primer

<400> SEQUENCE: 56
ctctcatatg acacaaacag tgataacacc c                                31

<210> SEQ ID NO 57
<211> LENGTH: 30
<212> TYPE: DNA
<213> ORGANISM: Artificial sequence
<220> FEATURE:
<223> OTHER INFORMATION: PCR primer

<400> SEQUENCE: 57
ctctcatatg ccacgttatt cttctccgag                                  30

<210> SEQ ID NO 58
<211> LENGTH: 23
<212> TYPE: DNA
<213> ORGANISM: Artificial sequence
<220> FEATURE:
<223> OTHER INFORMATION: PCR primer

<400> SEQUENCE: 58
ctctcatatg accgctgctc ccg                                         23

<210> SEQ ID NO 59
<211> LENGTH: 28
<212> TYPE: DNA
<213> ORGANISM: Artificial sequence
<220> FEATURE:
<223> OTHER INFORMATION: PCR primer

<400> SEQUENCE: 59
ctctcatatg ttatagggtg tccgggtc                                    28

<210> SEQ ID NO 60
<211> LENGTH: 32
<212> TYPE: DNA
<213> ORGANISM: Artificial sequence
<220> FEATURE:
<223> OTHER INFORMATION: PCR primer

<400> SEQUENCE: 60
ctctcatatg aatgtgacta gcttaagctt cc                               32

<210> SEQ ID NO 61
<211> LENGTH: 29
<212> TYPE: DNA
<213> ORGANISM: Artificial sequence
<220> FEATURE:
<223> OTHER INFORMATION: PCR primer

<400> SEQUENCE: 61
ctctcatatg tcactggcaa attgctcgc                                   29

<210> SEQ ID NO 62
<211> LENGTH: 25
<212> TYPE: DNA
<213> ORGANISM: Artificial sequence
<220> FEATURE:
<223> OTHER INFORMATION: PCR primer

<400> SEQUENCE: 62
ctctcatatg agcgcgcagt ccgtg                                       25

```
<210> SEQ ID NO 63
<211> LENGTH: 30
<212> TYPE: DNA
<213> ORGANISM: Artificial sequence
<220> FEATURE:
<223> OTHER INFORMATION: PCR primer

<400> SEQUENCE: 63
ctctcatatg cagtttcatc tcgtggtctc                               30
```